US012709761B2

(12) United States Patent
Lowenthal

(10) Patent No.: US 12,709,761 B2

(45) Date of Patent: Aug. 18, 2026

(54) ENGINEERED ADENOVIRUS VECTORS AND USES THEREOF

(71) Applicant: Richard Lowenthal, San Diego, CA (US)

(72) Inventor: Richard Lowenthal, San Diego, CA (US)

( * ) Notice: Subject to any disclaimer, the term of this patent is extended or adjusted under 35 U.S.C. 154(b) by 713 days.

(21) Appl. No.: 18/060,776

(22) Filed: Dec. 1, 2022

(65) Prior Publication Data

US 2023/0279432 A1 Sep. 7, 2023

Related U.S. Application Data

(63) Continuation of application No. PCT/US2021/036409, filed on Jun. 8, 2021.

(60) Provisional application No. 63/037,153, filed on Jun. 10, 2020.

(51) Int. Cl.
*C12N 15/86* (2006.01)

(52) U.S. Cl.
CPC .... *C12N 15/86* (2013.01); *C12N 2710/10022* (2013.01); *C12N 2710/10043* (2013.01); *C12N 2710/10051* (2013.01)

(58) Field of Classification Search
None
See application file for complete search history.

(56) References Cited

U.S. PATENT DOCUMENTS

| | | | |
|---|---|---|---|
| 4,920,209 A | 4/1990 | Davis et al. | |
| 6,127,525 A | 10/2000 | Crystal et al. | |
| 7,094,398 B1 | 8/2006 | Lieber et al. | |
| 8,865,182 B2 | 10/2014 | Mayall et al. | |
| 8,926,987 B2 | 1/2015 | Peng et al. | |
| 9,732,359 B2 | 8/2017 | Peng et al. | |
| 2004/0106193 A1 | 6/2004 | Kay et al. | |
| 2007/0003923 A1 | 1/2007 | Nemerow et al. | |
| 2010/0196336 A1 | 8/2010 | Park et al. | |
| 2016/0289645 A1 | 10/2016 | Tufaro et al. | |
| 2016/0319304 A1* | 11/2016 | Brown | C12N 15/86 |
| 2021/0008134 A1* | 1/2021 | Kosai | A61K 48/005 |

FOREIGN PATENT DOCUMENTS

| | | |
|---|---|---|
| CN | 103146753 A | 6/2013 |
| EP | 1224310 A1 | 7/2002 |
| EP | 3150706 B1 | 7/2019 |
| JP | 2010119306 A | 6/2010 |
| WO | WO-2001025463 A1 | 4/2001 |
| WO | WO-2006127956 A2 | 11/2006 |
| WO | WO-2008010864 A2 | 1/2008 |
| WO | WO-2018118967 A1 | 6/2018 |
| WO | WO-2021252496 A1 | 12/2021 |

OTHER PUBLICATIONS

English translation of JP2010119306A (Year: 2010).*

Havunen et al, Oncolytic Adenoviruses Armed with Tumor Necrosis Factor Alpha and interleukin-2 Enable Successful Adoptive Cell Therapy, Mar. 2017, Moleculer Therapy: Oncolytics vol. 4, pp. 77-86 (Year: 2017).*

Farrera-Sal et al, Effect of Transgene Location, Transcriptional Control Elements and Transgene Features in Armed Oncolytic Adenoviruses, Cancers, 12(4), 1034, Apr. 22, 2020 (Year: 2020).*

Wu et al, An oncolytic adenovirus 11p vector expressing adenovirus death protein in the E1 region showed significant apoptosis and tumour-killing ability in metastatic prostate cells, Oncotarget, 2019, vol. 10, (No. 20), pp. 1957-1974 (Year: 2019).*

Ganesh, Shanthi. et al. Relaxin-expressing, fiber chimeric oncolytic adenovirus prolongs survival of tumor-bearing mice. Cancer research 67(9):4399-4407 (2007).

Suzuki, Takayuki. et al. Development of a recombinant adenovirus vector production system free of replication-competent adenovirus by utilizing a packaging size limit of the viral genome. Virus research 158(1-2):154-160 (2011).

Brunetti-Pierri, N. et al., "Helper-dependent adenoviral vectors for liver-directed gene therapy," Human Molecular Genetics, 2011;20:7-13.

Cao, C. et al., "Conserved fiber-penton base interaction revealed by nearly atomic resolution cryo-electron microscopy of the structure of adenovirus provides insight into receptor interaction," J Virol., 2012;86(22):12322-12329.

Cheng, P. et al., "Molecular Bases for Viral Selective Replication in Cancer Cells: Activation of CDK2 by Adenovirus-Induced Cyclin E," PLoS One, 2013;8(2):e57340.

Clontech pShuttle vector information, (Feb. 2, 2000). https://media.bcm.edu/documents/2015/92/pshuttlex.pdf.

Crystal, R.G., "Adenovirus: The First Effective In Vivo Gene Delivery Vector," Human Gene Therapy, 2014;25:3-11.

Dubensky, T.W., "(Re-)Engineering tumor cell-selective replicating adenoviruses: A step in the right direction toward systemic therapy for metastatic disease," Cancer Cell, 2002;1(4):307-309.

Gluzman, Y., "SV40-transformed simian cells support the replication of early SV40 mutants," Cell, 1981;23(1):175-182.

Heise, C. et al., "ONYX-015, an E1B gene-attenuated adenovirus, causes tumor-specific cytolysis and antitumoral efficacy that can be augmented by standard chemotherapeutic agents," Nature Medicine, 1997;3:639-645.

Heise, C. et al., "Replication-selective adenoviruses as oncolytic agents," The Journal of Clinical Investigation, 2000;105(7):847-851.

(Continued)

*Primary Examiner* — Allison M Fox
*Assistant Examiner* — Marisol Ann O'Neill
(74) *Attorney, Agent, or Firm* — WILSON SONSINI GOODRICH & ROSATI

(57) ABSTRACT

Disclosed herein relates to a replication competent recombinant adenovirus comprising restriction enzyme sites in an E3 region to insert a gene of interest. Also disclosed herein is a method for generating the replication competent recombinant adenovirus and a pharmaceutical composition comprising the adenovirus for use in treating a disease or a condition.

19 Claims, 1 Drawing Sheet

Specification includes a Sequence Listing.

(56) References Cited

OTHER PUBLICATIONS

Mathis, J.M. et al., "Oncolytic adenoviruses—selective retargeting to tumor cells," Oncogene, 2005;24:7775-7791.
Mizuguchi, H. et al., "A Simple Method for Constructing E1- and E1/E4-Deleted Recombinant Adenoviral Vectors," Human Gene Therapy, 1999;10(12):2013-2017.
Nicklin, S.A. et al., "The influence of adenovirus fiber structure and function on vector development for gene therapy," Molecular Therapy, 2005;12(3):384-393.
O'Shea, C.C. et al., "Late viral RNA export, rather than p53 inactivation, determines ONYX-015 tumor selectivity," Cancer Cell, 2004;6:611-623.
Reason, (Jun. 6, 2016), "A short list of potential target genes for Near-Future gene therapies aimed at slowing aging or compensating for Age-Related damage and decline," Fight Aging! https://www.fightaging.org/archives/2016/06/a-short-list-of-potential-target-genes-for-near-future-gene-therapies-aimed-at-slowing-aging-or-compensating-for-age-related-damage-and-decline.
Rux, J.J. et al., "Adenovirus structure," Human Gene Therapy, 2004;15:1167-1176.
Shayakhmetov, D.M. et al., "The Interaction between the Fiber Knob Domain and the Cellular Attachment Receptor Determines the Intracellular Trafficking Route of Adenoviruses," Journal of Virology, 2003;77(6):3712-3723.
Smith, T.J. et al., "Experimental Respiratory Infection with Type 4 Adenovirus Vaccine in Volunteers: Clinical and Immunological Responses," Journal of Infectious Diseases, 1970;122:239-248.
Tacket, C.O. et al., "Initial safety and immunogenicity studies of an oral recombinant adenohepatitis B vaccine," Vaccine, 1992;10:673-676.
Takafuji, E.T. et al., "Simultaneous Administration of Live, Enteric-Coated Adenovirus Types 4,7, and 21 Vaccines: Safety and Immunogenicity," The Journal of Infectious Diseases, 1979;140:48-53.
Tinsley, J.M. et al., "Amelioration of the dystrophic phenotype of mdx mice using a truncated utrophin transgene," Nature, 1996;384(6607):349-353.
Top, F.H. et al., "Immunization with Live Types 7 and 4 Adenovirus Vaccines. II. Antibody Response and Protective Effect against Acute Respiratory Disease due to Adenovirus Type 7," The Journal of Infectious Diseases, 1971;124(2):155-160.
Vincent, N. et al., "Long-term correction of mouse dystrophic degeneration by adenovirus-mediated transfer of minidystrophin gene," Nature Genetics, 1993;5:130-134.
Watanabe, M. et al., "A novel gene expression system strongly enhances the anticancer effects of a REIC/Dkk-3-encoding adenoviral vector," Oncology Reports, 2014;31(3):1089-1095.
Wold, W.S.M. et al., "Adenovirus Vectors for Gene Therapy, Vaccination and Cancer Gene Therapy," Curr. Gene, Ther., 2013;13(6):421-433.
International Search Report and Written Opinion issued in PCT/US2021/036409, mailed Oct. 18, 2021.
International Preliminary Report on Patentability issued in PCT/US2021/036409, dated Dec. 13, 2022.

* cited by examiner

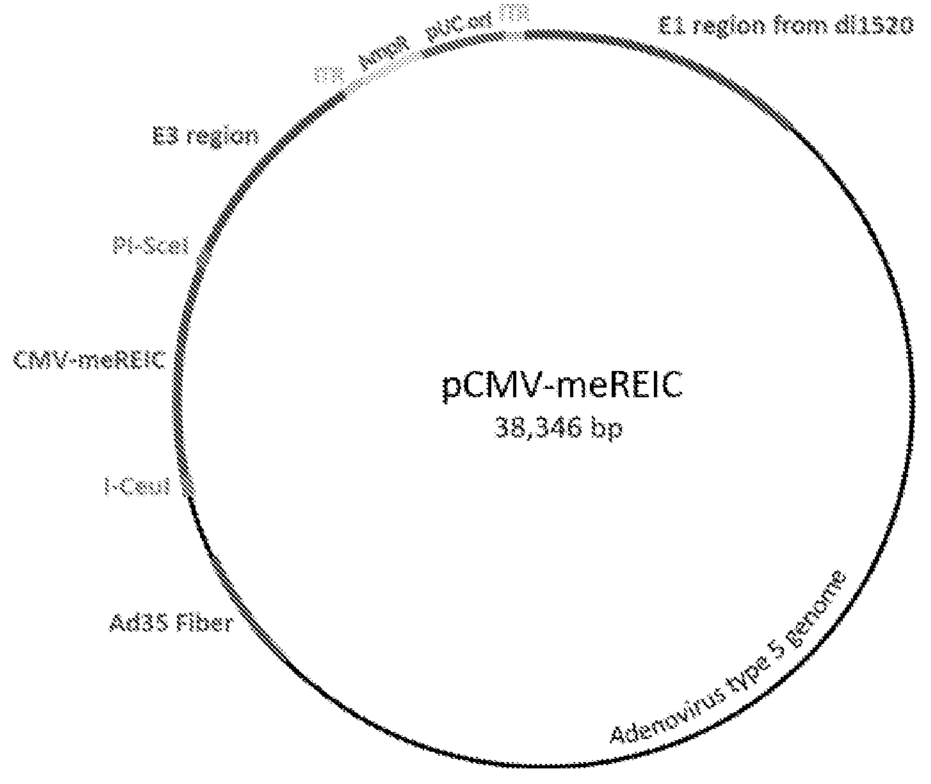
AmpR
pUC ori
E1 region from dl1520
E3 region
PI-SceI
CMV-meREIC
pCMV-meREIC
38,346 bp
I-CeuI
Ad35 Fiber
Adenovirus type 5 genome

SEQUENCE LISTING

```
Sequence total quantity: 3
SEQ ID NO: 1            moltype = DNA  length = 26
FEATURE                 Location/Qualifiers
misc_feature            1..26
                        note = Description of Artificial Sequence:
                         Syntheticoligonucleotide
source                  1..26
                        mol_type = other DNA
                        organism = synthetic construct
SEQUENCE: 1
taactataac ggtcctaagg tagcga                                       26

SEQ ID NO: 2            moltype = DNA  length = 39
FEATURE                 Location/Qualifiers
misc_feature            1..39
                        note = Description of Artificial Sequence:
                         Syntheticoligonucleotide
source                  1..39
                        mol_type = other DNA
                        organism = synthetic construct
SEQUENCE: 2
atctatgtcg ggtgcggaga aagaggtaat gaaatggca                         39
```

```
SEQ ID NO: 3            moltype = DNA  length = 4135
FEATURE                 Location/Qualifiers
misc_feature            1..4135
                        note = Description of Artificial Sequence:
                         Syntheticpolynucleotide
source                  1..4135
                        mol_type = other DNA
                        organism = synthetic construct
SEQUENCE: 3
taactataac ggtcctaagg tagcgaaagc tcagatctgg atctcccgat cccctatggt  60
cgactctcag tacaatctgc tctgatgccg catagttaag ccagtatctg ctccctgctt  120
gtgtgttgga ggtcgctgag tagtgcgcga gcaaaattta agctacaaca aggcaaggct  180
tgaccgacaa ttgcatgaag aatctgctta gggttaggcg ttttgcgctg cttcgcgatg  240
tacgggccag atatacgcgt tgacattgat tattgactag ttattaatag taatcaatta  300
cggggtcatt agttcatagc ccatatatgg agttccgcgt tacataactt acggtaaatg  360
gcccgcctgg ctgaccgccc aacgaccccc gcccattgac gtcaataatg acgtatgttc  420
ccatagtaac gccaataggg actttccatt gacgtcaatg ggtggactat ttacggtaaa  480
ctgcccactt ggcagtacat caagtgtatc atatgccaag tacgccccct attgacgtca  540
atgacggtaa atggcccgcc tggcattatg cccagtacat gaccttatgg gactttccta  600
cttggcagta catctacgta ttagtcatcg ctattaccat ggtgatgcgg ttttggcagt  660
acatcaatgg gcgtggatag cggtttgact cacggggatt tccaagtctc caccccattg  720
acgtcaatgg gagtttgttt tggcaccaaa atcaacggga ctttccaaaa tgtcgtaaca  780
actccgcccc attgacgcaa atgggcggta ggcgtgtacg gtgggaggtc tatataagca  840
gagctctctg gctaactaga gaacccactg cttactggct tatcgaaatt aatacgactc  900
actataggga gacccaagct ggctagcgtt taaacgggcc ctctagactc gagcggccgc  960
cactgtgctg gatgatccga gctcggtacc aagcttaagt ttaaaccgct gatcagcctc  1020
gactgtgcct tctagttgcc agccatctgt tgtttgcccc tcccccgtgc cttccttgac  1080
cctggaaggt gccactccca ctgtcctttc ctaataaaat gaggaaattg catcgcattg  1140
tctgagtagg tgtcattcta ttctgggggg tggggtgggg caggacagca agggggagga  1200
ttgggaagac aatagcaggc atgctgggga tgcggtgggc tctatggctt ctgaggcgga  1260
aagaaccagc agatctgcag atctgaattc atctatgtcg ggtgcggaga aagaggtaat  1320
gaaatggcat tatgggtatt atgggtctgc attaatgaat cggccaacgc gcggggagag  1380
gcggtttgcg tattgggcgc tcttccgctt cctcgctcac tgactcgctg cgctcggtcg  1440
ttcggctgcg gcgagcggta tcagctcact caaaggcggt aatacggtta tccacagaat  1500
caggggataa cgcaggaaag aacatgtgag caaaaggcca gcaaaaggcc aggaaccgta  1560
aaaaggccgc gttgctggcg tttttccata ggctccgccc ccctgacgag catcacaaaa  1620
atcgacgctc aagtcagagg tggcgaaacc cgacaggact ataaagatac caggcgtttc  1680
cccctggaag ctccctcgtg cgctctcctg ttccgaccct gccgcttacc ggatacctgt  1740
ccgcctttct cccttcggga agcgtggcgc tttctcaatg ctcacgctgt aggtatctca  1800
gttcggtgta ggtcgttcgc tccaagctgg gctgtgtgca cgaacccccc gttcagcccg  1860
accgctgcgc cttatccggt aactatcgtc ttgagtccaa cccggtaaga cacgacttat  1920
cgccactggc agcagccact ggtaacagga ttagcagagc gaggtatgta ggcggtgcta  1980
cagagttctt gaagtggtgg cctaactacg gctacactag aaggacagta tttggtatct  2040
gcgctctgct gaagccagtt accttcggaa aaagagttgg tagctcttga tccggcaaac  2100
aaaccaccgc tggtagcggt ggtttttttg tttgcaagca gcagattacg cgcagaaaaa  2160
aaggatctca agaagatcct ttgatctttt ctacggggtc tgacgctcag tggaacgaaa  2220
actcacgtta agggattttg gtcatgagat tatcaaaaag gatcttcacc tagatccttt  2280
tgatcctccg gcgttcagcc tgtgccacag ccgacaggat ggtgaccacc atttgcccca  2340
tatcaccgtc ggtactgatc ccgtcgtcaa taaaccgaac cgctacaccc tgagcatcaa  2400
actcttttat cagttggatc atgtcggcgg tgtcgcggcc aagacggtcg agcttcttca  2460
ccagaatgac atcaccttcc tccaccttca tcctcagcaa atccagccct tcccgatctg  2520
ttgaactgcc ggatgccttg tcggtaaaga tgcggttagc ttttacccct gcatctttga  2580
gcgctgaggt ctgcctcgtg aagaaggtgt tgctgactca taccaggcct gaatcgcccc  2640
atcatccagc cagaaagtga gggagccacg gttgatgaga gctttgttgt aggtggacca  2700
gttggtgatt ttgaactttt gctttgccac ggaacggtct gcgttgtcgg gaagatgcgt  2760
gatctgatcc ttcaactcag caaaagttcg atttattcaa caaagccgcc gtcccgtcaa  2820
gtcagcgtaa tgctctgcca gtgttacaac caattaacca attctgatta gaaaaactca  2880
tcgagcatca aatgaaactg caatttattc atatcaggat tatcaatacc atatttttga  2940
aaaagccgtt tctgtaatga aggagaaaac tcaccgaggc agttccatag gatggcaaga  3000
tcctggtatc ggtctgcgat tccgactcgt ccaacatcaa tacaacctat taatttcccc  3060
tcgtcaaaaa taaggttatc aagtgagaaa tcaccatgag tgacgactga atccggtgag  3120
aatggcaaaa gcttatgcat ttctttccag acttgttcaa caggccagcc attacgctcg  3180
tcatcaaaat cactcgcatc aaccaaaccg ttattcattc gtgattgcgc ctgagcgaga  3240
cgaaatacgc gatcgctgtt aaaaggacaa ttacaaacag gaatcgaatg caaccggcgc  3300
aggaacactg ccagcgcatc aacaatattt tcacctgaat caggatattc ttctaatacc  3360
tggaatgctg ttttcccggg gatcgcagtg gtgagtaacc atgcatcatc aggagtacgg  3420
ataaaatgct tgatggtcgg aagaggcata aattccgtca gccagtttag tctgaccatc  3480
tcatctgtaa catcattggc aacgctacct ttgccatgtt tcagaaacaa ctctggcgca  3540
tcgggcttcc catacaatcg atagattgtc gcacctgatt gcccgacatt atcgcgagcc  3600
catttatacc catataaatc agcatccatg ttggaattta atcgcggcct cgagcaagac  3660
gtttcccgtt gaatatggct cataacaccc cttgtattac tgtttatgta agcagacagt  3720
tttattgttc atgatgatat atttttatct tgtgcaatgt aacatcagag attttgagac  3780
acaacgtggc tttgttgaat aaatcgaact tttgctgagt tgaaggatca gatcacgcat  3840
cttcccgaca acgcagaccg ttccgtggca aagcaaaagt tcaaaatcac caactggtcc  3900
acctacaaca aagctctcat caaccgtggc tccctcactt tctggctgga tgatggggcg  3960
attcaggcct ggtatgagtc agcaacacct tcttcacgag gcagacctca gcgctagatt  4020
attgaagcat ttatcagggt tattgtctca tgagcggata catatttgaa tgtatttaga  4080
aaaataaaca aataggggtt ccgcgcacat ttccccgaaa agtgccacct gacgt       4135
```

ENGINEERED ADENOVIRUS VECTORS AND USES THEREOF

CROSS-REFERENCE TO RELATED APPLICATIONS

This application is a continuation of International Application No. PCT/US2021/036409, filed Jun. 8, 2021, which claims the benefit of U.S. Provisional Application No. 63/037,153, filed Jun. 10, 2020, all of which are incorporated by reference herein in their entirety.

SEQUENCE LISTING

The instant application contains a Sequence Listing which has been submitted electronically in XML format and is hereby incorporated by reference in its entirety. Said XML copy, created on Nov. 28, 2022, is named 57449-701.301_SL.xml txt and is 9,101 bytes in size.

BACKGROUND

Adenovirus vectors have been widely used for gene therapies and vaccine development to transfer heterologous immunogenic and/or therapeutic genes and more than 400 gene therapy trials have been or are being conducted with human adenovirus vectors. Adenovirus vectors have multiple advantages compared to other vectors, for example, they can be grown into high titer stable stocks, they infect non-dividing and dividing cells of different types, they are maintained in cells as an episome so that they do not affect the normal function of the host cells and their effects are not permanent, their genome can be modified to accommodate heterologous genes of up to about 8 kb, and nearly all clinical trials have indicated that they are safe and well tolerated. However, the use of adenovirus vectors in human therapy, including functional gene therapy, is still limited by the current methods of preparing these recombinant viruses. Particularly, current methods do not allow adenovirus vectors to be produced simply and rapidly. Accordingly, there remains a need for novel tools and methods for constructing recombinant adenoviruses that allows rapid and precise production of adenovirus vectors harboring genes of interest.

SUMMARY

Provided herein are compositions comprising recombinant adenovirus vectors and methods of using the same effective and rapid cloning and expression of genes of interest in host cells.

In an aspect, provided herein is a replication competent recombinant adenovirus comprising an I-CeuI restriction site, a PI-SceI restriction site, or a combination thereof in an E3 region. In some embodiments, the adenovirus further comprises an E1 region, wherein the E1 region comprises a same sequence as compared to a wild type adenovirus of the same serotype. In some embodiments, the E1 region comprises a partial deletion compared to a wild type adenovirus of the same serotype. In some embodiments, the E1 region of the adenovirus does not contain an insertion of a heterologous nucleotide sequence. In some embodiments, the E1 region comprises an E1B-55k deletion. In some embodiments, the E3 region comprises a partial deletion compared to a wild type adenovirus of the same serotype. In some embodiments, the E3 region comprises the I-CeuI restriction site and the PI-SceI restriction site. In some embodiments, the E3 region does not comprise a deletion as compared to a wild type adenovirus of the same serotype. In some embodiments, the replication competent adenovirus provided herein further comprises a modification in an E1a, E1b, E2, or E4 gene. In some embodiments, the adenovirus further comprises a polynucleotide sequence encoding a modified adenoviral fiber protein. In some embodiments, the modified adenoviral fiber protein is an Ad35 fiber tail protein. In some embodiments, the adenovirus is selected from the group consisting of adenovirus type 2, adenovirus type 4, adenovirus type 5, and adenovirus type 7. In some embodiments, the adenovirus is adenovirus type 5. In some embodiments, the adenovirus preferably replicates in a tumor cell as compared to a non-tumor cell. In some embodiments, the tumor cell comprises a mutation in a p53 gene, and wherein the tumor cell comprises a reduced level of the p53 gene expression as compared to a non-tumor cell. In some embodiments, any of the above described adenovirus comprises an I-CeuI restriction site and a PI-SceI restriction site in the E3 region. In some embodiments, the adenovirus further comprises a heterologous nucleotide sequence located between the I-CeuI restriction site and the PI-SceI restriction site. In some embodiments, the heterologous nucleotide sequence is cloned from a shuttle vector. In some embodiments, the shuttle vector is a pShuttleX vector. In some embodiments, the heterologous nucleotide sequence comprises a gene. In some embodiments, the heterologous nucleotide sequence comprises a gene encoding a cytokine, a chemokine, a checkpoint inhibitor, or an interleukin. In some embodiments, the heterologous nucleotide sequence comprises a gene encoding a REIC protein. In some embodiments, the heterologous nucleotide sequence comprises a CMV-REIC sequence. In some embodiments, the heterologous nucleotide sequence comprises a IL-2 gene sequence. In some embodiments, the adenovirus further comprises an exogenous promoter. In some embodiments, the exogenous promoter is operably linked to the E3 region, the E1 region, or the heterologous nucleotide sequence. In some embodiments, the exogenous promoter is a tissue specific promoter. In some embodiments, the exogenous promoter comprises a CAG, CMV or SGE promoter system.

In an aspect, provided herein is a pharmaceutical composition comprising the adenovirus as described in any one of the above embodiments and a pharmaceutically acceptable carrier. In some embodiments, the pharmaceutical composition further comprises a therapeutic agent. In some embodiments, the therapeutic agent is a chemotherapeutic agent.

In an aspect, provided herein is a kit for producing an oncolytic adenovirus, comprising a shuttle vector and the adenovirus as described in the above embodiments. In some embodiments, the shuttle vector is a pShuttleX vector.

In an aspect, provided herein is a host cell comprising the adenovirus as described in the above embodiments. In some embodiments, the host cell is a human cell. In some embodiments, the host cell is a tumor cell.

In an aspect, provided herein is a method for expressing a gene in a host cell, the method comprising contacting the host cell with an effective amount of the adenovirus as described in the above embodiments, thereby expressing the gene in the host cell.

In an aspect, provided herein is a method for treating a proliferative disorder in a subject in need thereof, comprising administering the adenovirus or the pharmaceutical composition as described in the above embodiments to the subject. In some embodiments, the proliferative disorder is a cancer. In some embodiments, the administering is in combination with one or more therapies selected from the group consisting of surgery, radiation, chemotherapy, immunotherapy, and hormone therapy.

In an aspect, provided herein is a method for generating a replication competent recombinant adenovirus comprising a heterologous nucleotide sequence, comprising: (a) cloning a heterologous nucleotide sequence into a shuttle vector; (b) digesting the shuttle vector in (a) with an I-CeuI restriction enzyme and a PI-SceI restriction enzyme to excise a fragment encompassing the heterologous nucleotide sequence; (c) digesting an adenovirus vector with the I-CeuI restriction enzyme and the PI-SceI restriction enzyme; (d) ligating the fragment encompassing the heterologous nucleotide sequence in (b) into the adenovirus vector in (c), thereby generating a recombinant adenoviral plasmid; (e) transfecting the recombinant adenoviral plasmid into a packaging cell; and (0 recovering the replication competent recombinant adenovirus from the packaging cell, wherein the adenovirus vector comprises an I-CeuI restriction site and a PI-SceI restriction site in an E3 region. In some embodiments, the adenovirus vector further comprises an E1 region comprising the same sequence as compared to a wild type adenovirus of the same serotype. In some embodiments, the adenovirus vector further comprises an E1 region comprising an E1B-55k deletion as compared to a wild type adenovirus of the same serotype. In some embodiments, the E3 region comprises a partial deletion compared to a wild type adenovirus of the same serotype. In some embodiments, the E3 region does not comprise a deletion as compared to a wild type adenovirus of the same serotype. In some embodiments, the E3 region comprises no modification other than the I-Ceu and the PI-SceI restriction sites as compared to a wild type adenovirus of the same serotype. In some embodiments, the adenovirus vector further comprises a modification in an E1a, E1b, E2, or E4 gene. In some embodiments, the adenovirus vector further comprises a polynucleotide sequence encoding a modified adenoviral fiber protein. In some embodiments, the modified adenoviral fiber protein is an Ad35 fiber tail protein. In some embodiments, the adenovirus vector is selected from the group consisting of adenovirus type 2 vector, adenovirus type 4 vector, adenovirus type 5 vector, and adenovirus type 7 vector. In some embodiments, the adenovirus vector is adenovirus type 5 vector. In some embodiments, the replication competent recombinant adenovirus preferably replicates in a tumor cell as compared to a non-tumor cell. In some embodiments, the tumor cell comprises a mutation in a p53 gene. In some embodiments, the tumor cell comprises reduced level of the p53 gene expression as compared to a non-tumor cell. In some embodiments, the shuttle vector is a pShuttleX vector. In some embodiments, the heterologous nucleotide sequence comprises a gene. In some embodiments, the gene encodes a protein selected from the group consisting of MAGE-1, MAGE-2, MAGE-3, CEA, Tyrosinase, midkine, BAGE, CASP-8, β-catenin, CA-125, CDK-1, ESO-1, gp75, gplOO, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orfl12, SART1, SART2, SART3, BRAP, RTN4, GLEA2, T KS2, KIAA0376, ING4, HSPH1, C13orf24, RBPSUH, C6orfl53, KTR, NSEP1, U2AF1L, CY L2, TPR, SOX2, GOLGA, BMI1, COX-2, EGFRvIII, EZH2, LICAM, Livin, MRP-3, Nestin, OLIG2, ART1, ART4, B-cyclin, Glil, Cav-1, cathepsin B, CD74, E-cadherin, EphA2/Eck, Fra-l/Fosll, GAGE-1, Ganglioside/GD2, GnT-V, β1,6-N, Ki67, Ku70/80, PROX1, PSCA, SOX10, SOX11, Survivin, UPAR, Mesothelin, and WT-1, or an epitope thereof. In some embodiments, the gene encodes a cytokine, a chemokine, a checkpoint inhibitor, or an interleukin. In some embodiments, the heterologous nucleotide sequence comprises a REIC gene sequence. In some embodiments, the heterologous nucleotide sequence comprises a IL-2 sequence. In some embodiments, the adenovirus vector further comprises an exogenous promoter. In some embodiments, the exogenous promoter is operably linked to the E3 region, the E1 region, or the heterologous nucleotide sequence. In some embodiments, the exogenous promoter is a tissue specific promoter. In some embodiments, the exogenous promoter comprises a CAG, CMV or SGE promoter system.

In an aspect, provided herein is a polynucleotide sequence comprising an E3 region of an adenovirus, wherein the E3 region comprises an I-CeuI restriction site, a PI-SceI restriction site, or a combination thereof. In some embodiments, the E3 region comprises the I-CeuI restriction site and the PI-SceI restriction site.

In an aspect, provided herein is a modified E3 region of an adenovirus, wherein the modified E3 region comprises an I-CeuI restriction site, a PI-SceI restriction site, or a combination thereof. In some embodiments, the modified E3 region comprises the I-CeuI restriction site and the PI-SceI restriction site.

INCORPORATION BY REFERENCE

All publications herein are incorporated by reference to the same extent as if each individual publication or patent application was specifically and individually indicated to be incorporated by reference. The following description includes information that may be useful in understanding the present disclosure. It is not an admission that any of the information provided herein is prior art or relevant to the presently claimed subject matter, or that any publication specifically or implicitly referenced is prior art.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 1 depicts a schematic representation of construct design of an exemplary recombinant adenovirus vector.

DETAILED DESCRIPTION

Certain specific details of this description are set forth in order to provide a thorough understanding of various embodiments. However, one skilled in the art will understand that the present disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods, and materials are described below.

Definitions

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

The term "about" or "approximately" can mean within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and more preferably within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures. To facilitate an understanding of the present disclosure, a number of terms and phrases are defined below.

The terms "nucleotide sequence," "nucleic acid sequence," "polynucleic acid sequence," and any grammatical equivalents thereof are used herein interchangeably and have the identical meaning herein and refer to preferably DNA or RNA. The terms "nucleic acid sequence," "nucleotide sequence," and "nucleotide acid sequence" are used synonymous with the term "polynucleotide sequence." A nucleic acid sequence can be a polymer comprising or consisting of nucleotide monomers, which are covalently linked to each other by phosphodiester-bonds of a sugar/phosphate-backbone. The term "nucleic acid sequence" also encompasses modified nucleic acid sequences, such as base-modified, sugar-modified, or backbone-modified etc., DNA or RNA.

The term "heterologous nucleotide sequence" and its grammatical equivalents as used herein can refer to a nucleic acid or nucleotide sequence that comprises nucleic acid or nucleotide sequence that is adenoviral in origin (e.g., from another adenoviral serotype) or non-adenoviral in origin (e.g., from another organism such as human). In one example, an adenoviral nucleotide sequence encoding a fiber protein from one serotype (e.g., Ad35) can be integrated or inserted into an adenoviral vector generated from a different serotype (e.g., Ad5). In another example, a nucleotide sequence encoding a human gene can be integrated or inserted into an adenoviral vector.

The term "recombinant," "engineered," and their grammatical equivalents as used herein in the context of proteins or nucleic acids can refer to proteins or nucleic acids that do not occur in nature but are the products of human engineering. The term "recombinant" or "engineered" may refer to one or more alterations of a nucleic acid, e.g., the nucleic acid within an organism's genome or protein. The term "recombinant" or "engineered" can also refer to alterations, additions, and/or deletion of genes. For example, in some embodiments, a recombinant adenovirus can comprise an amino acid or nucleotide sequence that comprises at least one, at least two, at least three, at least four, at least five, at least six, or at least seven mutations or modifications as compared to any naturally occurring adenoviral amino acid or nucleotide sequence.

The term "subject" or "patient" encompasses mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like.

"Administering" and its grammatical equivalents as used herein can refer to providing one or more replication competent recombinant adenovirus or pharmaceutical compositions described herein to a subject or a patient. By way of example and without limitation, "administering" can be performed by intravenous (i.v.) injection, sub-cutaneous (s.c.) injection, intradermal (i.d.) injection, intraperitoneal (i.p.) injection, intramuscular (i.m.) injection, intravascular injection, infusion (inf.), oral routes (p.o.), topical (top.) administration, or rectal (p.r.) administration. One or more such routes can be employed. Parenteral administration can be, for example, by bolus injection or by gradual perfusion over time.

The terms "treat," "treating," or "treatment," and its grammatical equivalents as used herein, can include alleviating, abating, or ameliorating at least one symptom of a disease or a condition, preventing additional symptoms, inhibiting the disease or the condition, e.g., arresting the development of the disease or the condition, relieving the disease or the condition, causing regression of the disease or the condition, relieving a condition caused by the disease or the condition, or stopping the symptoms of the disease or the condition either prophylactically and/or therapeutically.

The terms "pharmaceutical composition" and its grammatical equivalents as used herein can refer to a mixture or solution comprising a therapeutically effective amount of an active pharmaceutical ingredient together with one or more pharmaceutically acceptable excipients, carriers, and/or a therapeutic agent to be administered to a subject, e.g., a human in need thereof.

The term "pharmaceutically acceptable" and its grammatical equivalents as used herein can refer to an attribute of a material which is useful in preparing a pharmaceutical composition that is generally safe, non-toxic, and neither biologically nor otherwise undesirable and is acceptable for veterinary as well as human pharmaceutical use. "Pharmaceutically acceptable" can refer a material, such as a carrier or diluent, which does not abrogate the biological activity or properties of the compound, and is relatively nontoxic, i.e., the material may be administered to a subject without causing undesirable biological effects or interacting in a deleterious manner with any of the components of the pharmaceutical composition in which it is contained.

The term "proliferative disorder" and its grammatical equivalents as used herein can refer to a disorder or a disease related to rapid growth of a cell. For example, a lymphoproliferative disorder is a disease caused by malignant or abnormal growth/proliferation of lymphoid cells and cells from reticuloendothelial system. For example, a myeloproliferative disorder is a disease caused by malignant or abnormal growth/proliferation of bone marrow cells including those that give rise to red blood cells, granulocytes, and platelets.

The term "cancer" and its grammatical equivalents as used herein can refer to a hyperproliferation of cells whose unique trait—loss of normal controls—results in unregulated growth, lack of differentiation, local tissue invasion, and metastasis. With respect to the inventive methods, the cancer can be any cancer, including any of acute lymphocytic cancer, acute myeloid leukemia, alveolar rhabdomyosarcoma, bladder cancer, bone cancer, brain cancer, breast cancer, cancer of the anus, anal canal, rectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer, and/or urinary bladder cancer. As used herein, the term "tumor" refers to an abnormal growth of cells or tissues, e.g., of malignant type or benign type.

The term "tumor antigen" and its grammatical equivalents as used herein can refer to an epitope or antigenic determinant region that is not present in a reference, such as a non-diseased cell, e.g., a non-cancerous cell or a germline cell, but is found in a diseased cell, e.g., a cancer cell. This includes a "neoepitope" of which a corresponding epitope is found in a normal non-diseased cell or a germline cell but, due to one or more mutations in a diseased cell, e.g., a cancer cell, the sequence of the epitope is changed.

The term "tumor repressor" and its grammatical equivalents as used herein can refer to a gene or a product, e.g., RNA or protein, of the gene that regulates and controls cell growth, e.g., replication and/or division. A mutation(s) in tumor repressor genes can lead to cancer.

Adenovirus Vectors

Provided herein are recombinant adenovirus vectors comprising nucleotide sequences derived from adenoviruses. As used herein, an adenovirus is intended to encompass all adenoviruses, including but not limited to all members and/or serotypes of the known seven species (or group) classified as A to G, including but not limited to the Atadenovirus, Mastadenovirus, and Aviadenovirus genera. Adenoviruses are nonenveloped large DNA viruses having linear and non-segmented genomes. In certain embodiments, an adenovirus comprises an inverted terminal repeat (ITR) at each end and a packaging signal next to the ITR on the 5' end. In certain embodiments, an adenovirus genome is about 26-46 kb and contains about 23-46 protein coding genes. In particular embodiments, an adenovirus genome comprises genes organized in transcription units: E1A, E1B, E2A, E2B, E3, and E4 transcription units are transcribed early (thus, "E") in the viral reproductive cycle and involved in replication and in regulation of transcription; and L1, L2, L3, L4, and L5 are transcribed later (thus, "L") in the viral reproductive cycle and involved in making components of the viral capsid or assembling the capsid. The E1 early region, containing E1A and E1B, is located at the 5' end of the adenovirus genome and encodes proteins that participate very early in the viral cycle and are essential to the expression of almost all the other genes of the adenovirus. In particular, the E1A transcription unit encodes proteins that transactivate the transcription of the other viral genes, inducing S-phase upon cellular infection by promoting transcription from the E1B, E2A, E2B, E3, and E4 regions and the L1, L2, L3, L4, and L5 regions. The E1B transcription unit encodes proteins that inhibit cellular apoptosis. The E3 transcriptional unit encodes proteins involved in invasion of the host cell immune response and prevention of infected cells from elimination.

The adenoviral infectious cycle takes place in 2 steps: the early phase that permits production of the regulatory proteins and proteins involved in the replication and transcription of the viral DNA prior to the replication initiation, and the late phase that permits the synthesis of the structural proteins. The adenovirus can enter the host cell through adenovirus fiber interaction with a cell surface receptor, such as coxsackievirus and adenovirus receptor (CAR) or CD46, and secondary integrin receptors (e.g., $\alpha v\beta_{3-5}$). The viral DNA associated with viral proteins necessary for the first steps of the replication cycle enters the nucleus of the infected cells for the transcription to be initiated. The adenoviral DNA replication takes place in the nucleus of the infected cells and does not require cell replication. New viral particles or virions are assembled after which they are released from the infected cells and can infect other host cells. Branton and Marcellus (2011) "Adenoviruses" Fundamentals of Molecular Virology (2ed), Crystal Human Gene Therapy 25:3-11.

Adenoviral genome and core proteins are surrounded by a complex protein capsid, which is composed of seven structural proteins: II (hexon), III (penton), Ma, IV (fiber), VI, VII, and IX. The capsid has icosahedral shape and the faces are composed of 240 hexon capsomeres and 12 penton capsomeres. Each of 240 hexon capsomeres is a trimer of identical hexon proteins and 12 hexon capsomeres lie at each of the 20 facets. Each of 12 penton capsomeres is a pentamer of penton proteins and lies at each of the 12 vertices. Each vertex has a long fiber which is a trimer of fiber protein that protrudes outward and forms a knob at the protruding end. Each penton capsomer is bound to six adjacent hexon capsomeres and a fiber. In addition, a few minor proteins bind in the grooves between the hexon and penton capsomeres, guiding the assembly of the capsid and gluing the entire structure together. The hexon and the fiber proteins are determinants of serotype specificity and are the main antigenic determinants of an adenovirus. Rux and Burnett (2004) "Adenovirus Structure" Human Gene Therapy 15:1167-1176.

In some embodiments, an adenovirus described herein comprises a genome comprising nucleotide sequences encoding a fiber protein or a fiber tail. In some embodiments, the fiber protein or fiber tail comprises a knob domain, a shaft domain, and a tail domain. Without wishing to be bound by any theory, the fiber tail initiates the attachment of an adenovirus to a cell by attaching to a primary receptor of the cell (e.g., coxsackievirus and adenovirus receptor and CD46). Then, the penton protein engages with a secondary receptor such as integrin through its loop region, which contains an Arg-Gly-Asp (RGD) motif, to trigger virus internalization. This well-orchestrated attachment of the adenovirus to a cell that involves the fiber and penton proteins is structurally conserved among the different adenovirus serotypes. For example, Ad5F35 capsid comprising an adenovirus type 5 (Ad5) capsid pseudotyped with an adenovirus type 35 (Ad35) fiber has a similar fiber-penton base interaction to that of an Ad5 (Cao, et al., (2012) "Conserved fiber-penton base interaction revealed by nearly atomic resolution cryo-electron microscopy of the structure of adenovirus provides insight into receptor interaction" J Virol. 86(22): 12322-12329). As the cell surface receptor used for entering a cell is different depending on the serotype of an adenovirus, which could affect the adenoviral tropism of a specific serotype, modification of a fiber protein could provide a highly efficient and specific gene delivery using an adenovirus vector by re-directing the tropism of the adenovirus. Nicklin, et al., (2005) "The influence of adenovirus fiber structure and function on vector development for gene therapy" Mol. Ther. 12(3): 384-393; Shayakhmetov, et al., (2003) "The Interaction between the Fiber Knob Domain and the Cellular Attachment Receptor Determines the Intracellular Trafficking Route of Adenoviruses" J. Virol. 77(6): 3712-3723.

In some embodiments, provided herein is an adenovirus vector or an adenoviral vector comprising a wild type, a mutant, and/or a recombinant adenovirus genome, as well as adenoviruses comprising such a genome. In some embodiments, an adenovirus vector can be derived from any members of the known species (or group) and can comprise all or a part of the genome of any adenoviral serotype, as well as combinations thereof (i.e., hybrid genomes). Examples include, but are not limited to, adenovirus type 2 (group C adenovirus), adenovirus type 4 (group E adenovirus), adenovirus type 5 (group C adenovirus), and adenovirus type 7 (group B adenovirus). In some embodiments, an adenovirus can be categorized into a type or a serotype using a classification system based on molecular, immunological, and functional criteria. There are at least 57 serotypes of human adenoviruses. In some embodiments, recombinant adenovirus vectors have been designed and modified to encode and express heterologous genes and antigens for the purpose of gene therapy and vaccination. In some embodiments, adenovirus vectors may have deletions (e.g., E1A, E1B, E3, or E4) in their genomes. For example, E1 genes may be deleted to prevent replication in a host cell, which has been considered safer for administration to human subjects. In certain embodiments, an adenovirus is defective for replication due to deletions and proteins encoded by the deleted E1 genes may be supplied in trans for the virus to replicate. In another example, an E3 gene, which is involved in modulating the immune response of infected cells and not essential for virus production or growth, can be deleted to increase packaging capacity for an expression cassette of a heterologous gene. In this example, the deletions can allow insertion of an expression cassette of up to 7-8 kb comprising a promoter, a heterologous gene, and a polyadenylation (poly A) signal. In some embodiments, the adenovirus vector can be packaged in a packaging cell line that expresses the E1 region (e.g., HEK 293 cells, PER.C6 cells, 911-E4 cells, or N52.E6 cells) to provide all the components necessary for replication and packaging (Brunetti-Pierr and Ng (2011) "Helper-dependent adenoviral vectors for liver-directed gene therapy" Hum Mol Genet. 20:7-13).

In some embodiments, a recombinant adenovirus provided herein is capable of replicating within a host cell. For example, a replication competent adenovirus is able to replicate its genome after entering a host cell. In some embodiments, a recombinant adenovirus provided herein comprises reduced ability to replicate in a host cell. In some embodiments, a recombinant adenovirus provided herein may not have the ability to replicate in a host cell. A replication competent adenovirus may comprise different genomic elements as compared to a replication incompetent adenovirus. For example, a replication competent adenovirus may have an intact E1 region. In some embodiments, the replication competent adenovirus may have an intact E1A and/or E1B gene maintained in the genome whereas a replication defective adenovirus vectors have E1A and/or E1B genes deleted. In some embodiments, E1A and E1B genes are replaced by an expression cassette with a high activity promoter (e.g., cytomegalovirus immediate early (CMV) promoter, rous sarcoma virus long terminal repeat (RSV) promoter, etc.) that can drive expression of a heterologous gene inserted in the adenovirus vector. In an aspect, provided herein are recombinant adenovirus vectors that comprise one or more restriction sites in an E3 region and an E1 region that allows the adenovirus to retain replication competence. The E1 region may be intact as compared to a wild type adenovirus of the same serotype, or maybe modified to confer selective replication competence. In some embodiments, the recombinant adenovirus vector comprises an intact E1 region. In some embodiments, the recombinant adenovirus vector comprises an E3 region comprising one or more restriction sites, for example I-CeuI and/or PI-SceI restriction sites, and selectively replicates in cancer cells and not in normal cells. In some embodiments, the E3 region is otherwise intact as compared to a wild type adenovirus of the same serotype other than the one or more restriction sites. In some embodiments, the E3 region comprises a deletion.

In some embodiments, a recombinant adenovirus provided herein may conditionally replicate in a host cell. In some embodiments, a recombinant adenovirus provided herein selectively replicates in a certain host cell. In some embodiments, the host cell is a cancer cell. In some embodiments, the recombinant adenovirus replicates preferentially in cancer cells compared to non-cancer cells. In some embodiments, the recombinant adenovirus comprises a tumor- or tissue-specific promoter to limit the expression of the E1A gene to tumor cells or tumor tissues. In some embodiments, the recombinant adenovirus comprises tumor- or tissue-specific promoter sequences in replacement of endogenous viral promotor sequences to restrict adenoviral replication to a particular target tissue. For example, a prostate-specific antigen gene (PSA) promoter/enhancer element can be inserted upstream of the E1A gene so that viral replication may correlate with the level of PSA expression in a host cell. Non-limiting examples of tumor- or tissue-specific promotor/enhancer that can be used to drive E1 A expression selectively in specific tumors/carcinomas include an alpha fetoprotein (AFP), a carcinoembryonic antigen (CEA), mucin 1 (MUC1), and others. In some embodiments, the recombinant adenovirus comprises a second tumor- or tissue-specific promoter/enhancer inserted upstream of E1B region to improve selectivity. Selective replication of adenovirus in cancer cells are further described in Heise, et al., (2000) J Clin Invest. 105(7):847-851, Cheng, et al., (2013) PLoS One. 8(2):e57340, Dubensky (2002) Cancer Cell. 1(4):307-309, Mathis, et al. (2005) Oncogene. 24:7775-7791, each of which is incorporated herein by reference in its entirety.

In some embodiments, the recombinant adenovirus provided herein selectively replicates in cancer cells. Non-limiting examples of cancer cells include carcinoma, leukemia, lymphoma, myeloma, sarcoma, melanoma, mesothelioma, and cancers of central nervous system such as brain tumor. Additional examples of cancer cells include, but are not limited to, cells of Acute Lymphoblastic Leukemia (ALL), Acute Myeloid Leukemia (AML), Adrenocortical Carcinoma, AIDS-Related Cancers, Kaposi Sarcoma (Soft Tissue Sarcoma), AIDS-Related Lymphoma (Lymphoma), Primary CNS Lymphoma (Lymphoma), Anal Cancer, Appendix Cancer Astrocytomas, brain tumor, Atypical Teratoid/Rhabdoid Tumor, Brain tumor, Basal Cell Carcinoma of the Skin (Cancer), Bile Duct Cancer, Bladder Cancer, Bone Cancer including Ewing Sarcoma and Osteosarcoma and Malignant Fibrous Histiocytoma, Breast Cancer, Bronchial Tumors (Lung Cancer), Burkitt Lymphoma, Non-Hodgkin Lymphoma, Carcinoid Tumor (Gastrointestinal), Cardiac (Heart) Tumors, Atypical Teratoid/Rhabdoid Tumor, Medulloblastoma and Other CNS Embryonal Tumors, Germ Cell Tumor, Primary CNS Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma—see Lymphoma (Mycosis Fungoides and Sézary Syndrome), Ductal Carcinoma In Situ (DCIS), Embryonal Tumors, Medulloblastoma, Endometrial Cancer (Uterine Cancer), Ependymoma, Esophageal Cancer, Esthesioneuroblastoma (Head and Neck Cancer), Ewing Sarcoma (Bone Cancer), Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Osteosarcoma, Gallbladder Cancer, Gastric (Stomach) Cancer, Gastrointestinal Carcinoid Tumor, Gastrointestinal Stromal Tumors (GIST) (Soft Tissue Sarcoma), Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis, Langerhans Cell, Hodgkin Lymphoma, Hypopharyngeal Cancer (Head and Neck Cancer), Intraocular Melanoma, Islet Cell Tumors, Pancreatic Neuroendocrine Tumors, Kaposi Sarcoma (Soft Tissue Sarcoma), Kidney (Renal Cell) Cancer, Langerhans Cell Histiocytosis, Laryngeal Cancer (Head and Neck Cancer), Lip and Oral Cavity Cancer, Liver Cancer, Lung Cancer (Non-Small Cell, Small Cell, Pleuropulmonary Blastoma, and Tracheobronchial Tumor), Malignant Fibrous Histiocytoma of Bone and Osteosarcoma, Intraocular Melanoma, Merkel Cell Carcinoma (Skin Cancer), Mesothelioma, Metastatic Squamous Neck Cancer with Occult Primary (Head and Neck Cancer), Midline Tract Carcinoma With NUT Gene Changes, Mouth Cancer (Head and Neck Cancer), Multiple Endocrine Neoplasia Syndromes, Multiple Myeloma/Plasma Cell Neoplasms, Mycosis Fungoides (Lymphoma), Myelodysplastic Syndromes, Myelodysplastic/Myeloproliferative Neoplasms, Chronic Myelogenous Leukemia (CML), Acute Myeloid Leukemia (AML), Chronic Myeloproliferative Neoplasms, Nasal Cavity and Paranasal Sinus Cancer (Head and Neck Cancer), Nasopharyngeal Cancer (Head and Neck Cancer), Neuroblastoma, Non-Small Cell Lung Cancer, Oral Cancer, Lip and Oral Cavity Cancer and Oropharyngeal Cancer (Head and Neck Cancer, Osteosarcoma and Malignant Fibrous Histiocytoma of Bone, Ovarian Cancer, Pancreatic Cancer, Pancreatic Neuroendocrine Tumors (Islet Cell Tumors), Papillomatosis, Paraganglioma, Paranasal Sinus and Nasal Cavity Cancer (Head and Neck Cancer), Parathyroid Cancer, Penile Cancer, Pharyngeal Cancer (Head and Neck Cancer), Pheochromocytoma, Pituitary Tumor, Plasma Cell Neoplasm/Multiple Myeloma, Pleuropulmonary Blastoma (Lung Cancer), Primary Central Nervous System (CNS) Lymphoma, Primary Peritoneal Cancer, Prostate Cancer, Rectal Cancer, Renal Cell (Kidney) Cancer, Retinoblastoma, Rhabdomyosarcoma (Soft Tissue Sarcoma), Salivary Gland Cancer (Head and Neck Cancer), Vascular Tumors (Soft Tissue Sarcoma), Ewing Sarcoma (Bone Cancer), Kaposi Sarcoma (Soft Tissue Sarcoma), Osteosarcoma (Bone Cancer), Soft Tissue Sarcoma, Uterine Sarcoma, Sezary Syndrome (Lymphoma), Skin Cancer, Small Cell Lung Cancer, Small Intestine Cancer, Soft Tissue Sarcoma, Squamous Cell Carcinoma of the Skin, Squamous Neck Cancer with Occult Primary, Stomach (Gastric) Cancer, T-Cell Lymphoma (Mycosis Fungoides and Sezary Syndrome), Testicular Cancer, Throat Cancer (Head and Neck Cancer), Nasopharyngeal Cancer, Oropharyngeal Cancer, Hypopharyngeal Cancer, Thymoma and Thymic Carcinoma, Thyroid Cancer, Tracheobronchial Tumors (Lung Cancer), Transitional Cell Cancer of the Renal Pelvis and Ureter (Kidney (Renal Cell) Cancer), Ureter and Renal Pelvis, Transitional Cell Cancer (Kidney (Renal Cell) Cancer), Urethral Cancer, Endometrial Uterine Cancer, Uterine Sarcoma, Vaginal Cancer, Vulvar Cancer, Wilms Tumor, etc.

In some embodiments, the recombinant adenovirus comprises a deletion of genes that are critical for efficient viral replication in normal cells but not in tumor cells. In some embodiments, the replication competent adenovirus lacks the gene coding for an E1B-55k protein. Additional description of E1B-55k protein and adenovirus replication in normal cells can be found in Heise, et al., (1997) Nature Med. 3:639-645, which is incorporated herein by reference in its entirety. In some embodiments, the E1B-55k protein can facilitate export of adenovirus mRNA from the nucleus. In some embodiments, cancer cells can provide the function of E1B-55k gene and the recombinant adenovirus lacking the E1B-55k gene can replicate in cancer cells but not in normal cells. Additional description of adenovirus replication in cancer cells and what makes it a great vector (oncolytic adenovirus) for gene therapies for cancer treatments are described in O'Shea, et al., (2004) Cancer Cell. 6:611-623), which is incorporated herein by reference in its entirety.

In some aspects, the replication competent recombinant adenovirus described herein may preferably replicate in a tumor cell as compared to a non-tumor cell. In some embodiments, the tumor cell comprises a mutation in a p53 gene. In some embodiments, the tumor cell comprises a reduced level of the p53 gene expression as compared to a non-tumor cell. In some embodiments, the p53 gene expression in a tumor cell is reduced by about 1%, 5%, 10%, 15%, 20%, 25%, 30%, 35%, 40%, 45%, 50%, 55%, 60%, 65%, 70%, 75%, 80%, 85%, 90%, or 95% compared to a non-tumor cell. In some embodiments, the p53 gene expression in a tumor cell is reduced by about 1% to about 95% compared to a non-tumor cell. In some embodiments, the p53 gene expression in a tumor cell is reduced by about 1% to about 10%, about 1% to about 20%, about 1% to about 30%, about 1% to about 40%, about 1% to about 50%, about 1% to about 60%, about 1% to about 70%, about 1% to about 80%, about 1% to about 90%, about 1% to about 95%, about 10% to about 20%, about 10% to about 30%, about 10% to about 40%, about 10% to about 50%, about 10% to about 60%, about 10% to about 70%, about 10% to about 80%, about 10% to about 90%, about 10% to about 95%, about 20% to about 30%, about 20% to about 40%, about 20% to about 50%, about 20% to about 60%, about 20% to about 70%, about 20% to about 80%, about 20% to about 90%, about 20% to about 95%, about 30% to about 40%, about 30% to about 50%, about 30% to about 60%, about 30% to about 70%, about 30% to about 80%, about 30% to about 90%, about 30% to about 95%, about 40% to about 50%, about 40% to about 60%, about 40% to about 70%, about 40% to about 80%, about 40% to about 90%, about 40% to about 95%, about 50% to about 60%, about 50% to about 70%, about 50% to about 80%, about 50% to about 90%, about 50% to about 95%, about 60% to about 70%, about 60% to about 80%, about 60% to about 90%, about 60% to about 95%, about 70% to about 80%, about 70% to about 90%, about 70% to about 95%, about 80% to about 90%, about 80% to about 95%, or about 90% to about 95% compared to a non-tumor cell. In some embodiments, the p53 gene expression in a tumor cell is reduced by about 1%, about 10%, about 20%, about 30%, about 40%, about 50%, about 60%, about 70%, about 80%, about 90%, or about 95% compared to a non-tumor cell. In some embodiments, the p53 gene expression in a tumor cell is reduced by at least about 1%, about 10%, about 20%, about 30%, about 40%, about 50%, about 60%, about 70%, about 80%, or about 90% compared to a non-tumor cell. In some embodiments, the p53 gene expression in a tumor cell is reduced by at most about 10%, about 20%, about 30%, about 40%, about 50%, about 60%, about 70%, about 80%, about 90%, or about 95% compared to a non-tumor cell.

The recombinant adenovirus preferentially replicating in cancer cells may be oncolytic adenovirus. In some embodiments, the recombinant adenovirus preferentially replicating in cancer cells destroys cancer cells through the natural process of lytic virus replication. In some embodiments, tumor antigens can be released from destroyed cancer cells and induce systemic anti-tumor immunity. In some embodiments, the recombinant adenovirus preferentially replicating in cancer cells may have cytotoxic effects. In some embodiments, the recombinant adenovirus preferentially replicating in cancer cells comprises one or more genes encoding cytotoxic viral proteins (e.g., the E3 11.6 adenovirus death protein and E4ORF4).

In an aspect, the present disclosure provides a replication competent recombinant adenovirus comprising polynucleotide elements that allows for cloning of heterologous genes or polynucleotide sequences. In some embodiments, the recombinant adenovirus provided herein comprises one or more restriction enzyme recognition sites, or restriction sites. In some embodiments, the recombinant adenovirus provided herein comprises a BamHI restriction site, an EcoRI restriction site, a HindIII restriction site, an I-CeuI restriction site, a NotI restriction site, a PI-SceI restriction site, a PstI restriction site, a XhoI restriction site, or a combination thereof. In some embodiments, the recombinant adenovirus comprises an I-CeuI restriction site, a PI-SceI restriction site, or a combination thereof. In a preferred embodiment, the recombinant adenovirus comprises an I-CeuI restriction site and a PI-SceI restriction site. In some embodiments, a restriction site is introduced into an E1 region of an adenovirus. In some embodiments, a restriction site is introduced into an E2 region of an adenovirus. In some embodiments, a restriction site is introduced into an E3 region. In some embodiments, a restriction site is introduced into an E4 region of an adenovirus. In some embodiments, a restriction site is introduced into an L1 region of an adenovirus. In some embodiments, a restriction site is introduced into an L2 region of an adenovirus. In some embodiments, a restriction site is introduced into an L3 region of an adenovirus. In some embodiments, a restriction site is introduced into an L4 region of an adenovirus. In some embodiments, a restriction site is introduced into an L5 region of an adenovirus.

The present disclosure provides an improvement to a recombinant adenovirus to which a heterologous nucleotide sequence comprising a gene of interest can be inserted without deleting the E3 region. An E3 region of the replication competent recombinant adenovirus described herein may be genetically modified to comprise an I-CeuI restriction site, a PI-SceI restriction site, or a combination thereof to allow insertion of a heterologous nucleotide sequence comprising a gene of interest. A replication competent recombinant adenovirus may comprise a E3 region that is modified, partially deleted, completely deleted, or with the full E3 sequence separated by restriction sites to allow for insertion of genes of interest. In some embodiments, the recombinant adenovirus comprises a modified E3 region where a part of the E3 region sequence is deleted. In some embodiments, the recombinant adenovirus comprises a modified E3 region where one or more restriction sites are introduced into the E3 region to allow for insertion of genes of interest, while the sequence of the E3 region is otherwise intact. A replication competent recombinant adenovirus described herein may comprise a modification in the E3 region but does not comprise a complete deletion of the E3 region. The modification of the E3 region to add an I-CeuI restriction site, a PI-SceI restriction site, or a combination thereof can allow insertion of the heterologous nucleotide sequence comprising a gene of interest using a shuttle vector, e.g., a pShuttle vector, that may comprise the same set of restriction sites. Thus, the present invention disclosed herein also relates to a method for generating a replication competent recombinant adenovirus described herein comprising a heterologous nucleotide sequence of interest. In an aspect, the recombinant adenovirus as described herein allows the adenovirus to maintain replication competency and intact genomic regions and sequences, for example, intact E1 region. Accordingly, in some embodiments, the replication competent recombinant adenovirus comprises one or more restriction sites in the E3 region and an intact E1 region, and selectively replicates in cancer cells.

In some aspects, adenovirus vectors described herein may be genetically modified versions of adenovirus. In some embodiments, the replication competent recombinant adenovirus described herein may comprise an I-CeuI restriction site in the E3 region. In some embodiments, the replication competent recombinant adenovirus described herein may comprise and a PI-SceI restriction site in the E3 region. In a preferred embodiment, the replication competent recombinant adenovirus described herein may comprise an I-CeuI restriction site and a PI-SceI restriction site in the E3 region. In some embodiments, the replication competent recombinant adenovirus comprising an I-CeuI restriction site and a PI-SceI restriction site in the E3 region further comprises a heterologous nucleotide sequence located between the I-CeuI restriction site and the PI-SceI restriction site.

In one aspect, provided herein, is a polynucleotide sequence comprising an E3 region of an adenovirus, wherein the E3 region comprises an I-CeuI restriction site, a PI-SceI restriction site, or a combination thereof. In some embodiments, the E3 region comprises the I-CeuI restriction site and the PI-SceI restriction site. In another aspect, provided herein, is a modified E3 region of an adenovirus, wherein the modified E3 region comprises an I-CeuI restriction site, a PI-SceI restriction site, or a combination thereof. In some embodiments, the modified E3 region comprises the I-CeuI restriction site and the PI-SceI restriction site.

In some embodiments, a recombinant adenovirus vector can further comprise an exogenous promoter. In some embodiments, the exogenous promoter is operably linked to the E3 region. In some embodiments, the exogenous promoter is operably linked to the E1 region. In some embodiments, the exogenous promoter is operably linked to a heterologous nucleotide sequence. In some embodiments, the exogenous promoter can be an inducible promoter, a cell specific promoter, a developmental specific promoter, or a tissue specific promoter. In some embodiments, the exogenous promoter is a tissue specific promoter. Examples of tissue specific promoters include, but are not limited to, a FABP promoter, an Lck promoter, a CamKII promoter, a CD19 promoter, a Keratin promoter, an Albumin promoter, an aP2 promoter, an insulin promoter, an MCK promoter, a MyHC promoter, a WAP promoter, or a Col2A promoter. In some embodiments, the exogenous promoter may be a CMV promoter, an RSV long terminal repeat (LTR) promoter, a simian virus 40 (SV40) promoter, a dihydrofolate reductase (DHFR) promoter, a beta-actin promoter, a phosphoglycerate kinase (PGK) promoter, or an elongation factor-1 alpha (EF-1 alpha) promoter. In some embodiments, the exogenous promoter comprises a promoter system comprising one or more promoters, enhancers, or regulatory sequences. For example, the exogenous promoter may comprise a cytomegalovirus early enhancer element, a first exon and first intron of chicken beta-actin gene, and a splice acceptor of rabbit beta-globin gene (the CAG promoter system). In some embodiments, the exogenous promoter comprises one or more translational enhancer sequence of human telomerase reverse transcriptase (hTERT), a simian virus 40 (SV40) enhancer sequence, and/or a CMV enhancer sequence (the SGE promoter system). Promoter systems as described in Watanabe et al. Ocol Rep. 2014 31(3): 1089-1095 is incorporated herein by reference in its entirety. In some embodiments, the exogenous promoter is a CMV promoter. In some embodiments, the promoter can comprise an enhancer region, a TATA box, and a transcription start point. In particular embodiments, the exogenous promoter comprises a CAG promoter system. In another embodiment, the exogenous promoter is a SGE promoter system.

Shuttle Vectors

Provided herein are compositions and methods using systems comprising recombinant adenovirus vectors for rapid cloning and construction for expression of heterologous polynucleotides, e.g., genes of interest. In some embodiments, an adenovirus vector provided herein comprises a heterologous polynucleotide sequence cloned from a second vector, for example, a shuttle vector. In some embodiments, a heterologous nucleotide sequence is cloned from a shuttle vector. A shuttle vector may be a vector or a plasmid constructed to propagate in multiple host species, e.g., cells from two different organisms. For example, a shuttle vector may comprise two origins of replication and two marker genes for selection, one for each organism. Clark and Pazdernik (2013) "Cloning Genes for Analysis" Molecular Biology (2ed) e83-e88. Shuttle vectors are well known in the art and a skilled artisan can choose any shuttle vector suitable for cloning the heterologous nucleotide sequence of interest. For example, a pShuttle vector can be used for cloning the heterologous nucleotide sequence of interest. pShuttle vector as described in Clontech, USA; Mizuguchi and Kay (1999) "A Simple Method for Constructing E1- And E1/E4-deleted Recombinant Adenoviral Vectors" Hum. Gene Ther. 10:2013-2017 is incorporated herein by reference in its entirety. pShuttle vector utilizes a ligation-based strategy to clone a gene-specific mammalian expression cassette to a recombinant adenovirus. The mammalian expression cassette in the pShuttle vector comprises the human cytomegalovirus (CMV) immediate early promoter/enhancer, a multiple cloning site (MCS), and the bovine growth hormone polyadenylation signal. The heterologous nucleotide sequence of interest can be inserted into the MCS of pShuttle using any of the unique restriction sites available in the pShuttle. The MCS comprises restriction sites of NheI, ApaI, XbaI, NotI, BstXI, KpnI, and AflII. pShuttle also comprises the pUC origin (pUC ori) and a kanamycin resistance gene (KAN$^r$) in the backbone for propagation and selection in *E. coli.*

The recombinant adenovirus vectors provided herein can comprise restriction sites for efficient and rapid cloning of one or more genes of interest from a shuttle vector. For example, a recombinant adenovirus vector can comprise restriction sites corresponding to restriction sites in a Shuttle vector. Gene expression cassettes, e.g., a mammalian expression cassette in the pShuttle vector is flanked by two unique restriction sites, I-CeuI and PI-SceI, and can be excised and ligated directly into a recombinant adenoviral vector or plasmid that comprises the I-CeuI and PI-SceI restriction sites in the E3 region. In some embodiments, the heterologous nucleotide sequence of interest can be inserted into the MCS of pShuttle using one or more of any of the restriction sites available. In some embodiments, the heterologous nucleotide sequence of interest can be inserted into the MCS of pShuttle using any combination of the restriction sites. In some embodiments, the heterologous nucleotide sequence of interest may comprise a start codon for proper promoter driven expression in mammalian cells. In some embodiments, the heterologous nucleotide sequence of interest may be cDNA of a gene of interest. Once the heterologous nucleotide sequence of interest is cloned into pShuttle, the recombinant pShuttle vector can be digested with I-CeuI and PI-SceI to excise the mammalian expression cassette and the excised cassette can be inserted into the recombinant adenoviral vector or plasmid comprising I-CeuI and PI-SceI restriction sites in the E3 region. In some embodiments, the I-CeuI recognition sequence comprises 5'-TAACTATAACGGTCCTAAGGTAGCGA-3' (SEQ ID NO: 1). In some embodiments, the PI-Sce I recognition sequence comprises 5'-ATCTATGTCGGGTGCGGAGAAAGAGGTAATGAAATGGCA-3' (SEQ ID NO: 2).

Recombinant DNA technology can be employed to clone a heterologous nucleotide sequence into a shuttle vector. These procedures are generally known in the art, as described generally in Sambrook et al., Molecular Cloning, A Laboratory Manual, Cold Spring Harbor Press, Cold Spring Harbor, N.Y. (1989).

In some embodiments, heterologous nucleotide sequence may be cloned from a shuttle vector. In some embodiments, the shuttle vector is a pShuttleX-IRES-GFP vector. In some embodiments, the shuttle vector is a pShuttleX vector. An exemplary sequence of a pShuttleX vector is provided below:

(SEQ ID NO: 3)

taactataacggtcctaaggtagcgaaagctcagatctggatctcccgatcccctatggtcgactctcagtacaatctgctctgatgccg catagttaagccagtatctgctccctgcttgtgtgttggaggtcgctgagtagtgcgcgagcaaaatttaagctacaacaaggcaaggcttgaccga caattgcatgaagaatctgcttagggttaggcgttttgcgctgcttcgcgatgtacgggccagatatacgcgttgacattgattattgactagttattaa tagtaatcaattacggggtcattagttcatagcccatatatggagttccgcgttacataacttacggtaaatggcccgcctggctgaccgcccaacga cccccgcccattgacgtcaataatgacgtatgttcccatagtaacgccaatagggactttccattgacgtcaatgggtggactatttacggtaaactg cccacttggcagtacatcaagtgtatcatatgccaagtacgccccctattgacgtcaatgacggtaaatggcccgcctggcattatgcccagtacat gaccttatgggactttcctacttggcagtacatctacgtattagtcatcgctattaccatggtgatgcggttttggcagtacatcaatgggcgtggatag cggtttgactcacggggatttccaagtctccaccccattgacgtcaatgggagtttgttttggcaccaaaatcaacgggactttccaaaatgtcgtaa caactccgccccattgacgcaaatgggcggtaggcgtgtacggtgggaggtctatataagcagagctctctggctaactagagaacccactgctt actggcttatcgaaattaatacgactcactatagggagacccaagctggctagcgtttaaacgggccctctagactcgagcggccgccactgtgct ggatgatccgagctcggtaccaagcttaagtttaaaccgctgatcagcctcgactgtgccttctagttgccagccatctgttgtttgcccctcccccgt gccttccttgaccctggaaggtgccactcccactgtcctttcctaataaaatgaggaaattgcatcgcattgtctgagtaggtgtcattctattctgggg ggtggggtggggcaggacagcaagggggaggattgggaagacaatagcaggcatgctggggatgcggtgggctctatggcttctgaggcgg aaagaaccagcagatctgcagatctgaattcatctatgtcgggtgcggagaaagaggtaatgaaatggcattatgggtattatgggtctgcattaat gaatcggccaacgcgcggggagaggcggtttgcgtattgggcgctcttccgcttcctcgctcactgactcgctgcgctcggtcgttcggctgcgg cgagcggtatcagctcactcaaaggcggtaatacggttatccacagaatcaggggataacgcaggaaagaacatgtgagcaaaaggccagcaa aaggccaggaaccgtaaaaaggccgcgttgctggcgtttttccataggctccgcccccctgacgagcatcacaaaaatcgacgctcaagtcaga ggtggcgaaacccgacaggactataaagataccaggcgtttccccctggaagctccctcgtgcgctctcctgttccgaccctgccgcttaccgga tacctgtccgcctttctcccttcgggaagcgtggcgctttctcaatgctcacgctgtaggtatctcagttcggtgtaggtcgttcgctccaagctgggc tgtgtgcacgaaccccccgttcagcccgaccgctgcgccttatccggtaactatcgtcttgagtccaacccggtaagacacgacttatcgccactg gcagcagccactggtaacaggattagcagagcgaggtatgtaggcggtgctacagagttcttgaagtggtggcctaactacggctacactagaa ggacagtatttggtatctgcgctctgctgaagccagttaccttcggaaaaagagttggtagctcttgatccggcaaacaaaccaccgctggtagcg gtggtttttttgtttgcaagcagcagattacgcgcagaaaaaaaggatctcaagaagatcctttgatcttttctacggggtctgacgctcagtggaacg aaaactcacgttaagggattttggtcatgagattatcaaaaaggatcttcacctagatccttttgatcctccggcgttcagcctgtgccacagccgaca ggatggtgaccaccatttgccccatatcaccgtcggtactgatcccgtcgtcaataaaccgaaccgctacaccctgagcatcaaactcttttatcagt tggatcatgtcggcggtgtcgcggccaagacggtcgagcttcttcaccagaatgacatcaccttcctccaccttcatcctcagcaaatccagccctt cccgatctgttgaactgccggatgccttgtcggtaaagatgcggttagcttttacccctgcatctttgagcgctgaggtctgcctcgtgaagaaggtg ttgctgactcataccaggcctgaatcgccccatcatccagccagaaagtgagggagccacggttgatgagagctttgttgtaggtggaccagttgg tgattttgaacttttgctttgccacggaacggtctgcgttgtcgggaagatgcgtgatctgatccttcaactcagcaaaagttcgatttattcaacaaag ccgccgtcccgtcaagtcagcgtaatgctctgccagtgttacaaccaattaaccaattctgattagaaaaactcatcgagcatcaaatgaaactgca atttattcatatcaggattatcaataccatatttttgaaaaagccgtttctgtaatgaaggagaaaactcaccgaggcagttccataggatggcaagat cctggtatcggtctgcgattccgactcgtccaacatcaatacaacctattaatttcccctcgtcaaaaataaggttatcaagtgagaaatcaccatgag tgacgactgaatccggtgagaatggcaaaagcttatgcatttctttccagacttgttcaacaggccagccattacgctcgtcatcaaaatcactcgca tcaaccaaaccgttattcattcgtgattgcgcctgagcgagacgaaatacgcgatcgctgttaaaaggacaattacaaacaggaatcgaatgcaac cggcgcaggaacactgccagcgcatcaacaatattttcacctgaatcaggatattcttctaatacctggaatgctgttttcccggggatcgcagtggt gagtaaccatgcatcatcaggagtacggataaaatgcttgatggtcggaagaggcataaattccgtcagccagtttagtctgaccatctcatctgta acatcattggcaacgctacctttgccatgtttcagaaacaactctggcgcatcgggcttcccatacaatcgatagattgtcgcacctgattgcccgac -continued

```
attatcgcgagcccatttatacccatataaatcagcatccatgttggaatttaatcgcggcctcgagcaagacgtttcccgttgaatatggctcataac

accccttgtattactgtttatgtaagcagacagttttattgttcatgatgatatatttttatcttgtgcaatgtaacatcagagattttgagacacaacg

tggctttgttgaataaatcgaacttttgctgagttgaaggatcagatcacgcatcttcccgacaacgcagaccgttccgtggcaaagcaaaagttcaaaa

tcaccaactggtccacctacaacaaagctctcatcaaccgtggctccctcactttctggctggatgatggggcgattcaggcctggtatgagtcagca

acaccttcttcacgaggcagacctcagcgctagattattgaagcatttatcagggttattgtctcatgagcggatacatatttgaatgtatttagaaaaa

taaacaaataggggttccgcgcacatttccccgaaaagtgccacctgacgt.
```

In some embodiments, a recombinant adenovirus vector can further comprise an exogenous promoter. In some embodiments, the exogenous promoter is operably linked to the E3 region. In some embodiments, the exogenous promoter is operably linked to the E1 region. In some embodiments, the exogenous promoter is operably linked to a heterologous nucleotide sequence. In some embodiments, the exogenous promoter can be an inducible promoter, a cell specific promoter, a developmental specific promoter, or a tissue specific promoter. In some embodiments, the exogenous promoter is a tissue specific promoter. Examples of tissue specific promoters include, but are not limited to, a FABP promoter, an Lck promoter, a CamKII promoter, a CD19 promoter, a Keratin promoter, an Albumin promoter, an aP2 promoter, an insulin promoter, an MCK promoter, a MyHC promoter, a WAP promoter, or a Col2A promoter. In some embodiments, the exogenous promoter may be selected from the group consisting of a CMV promoter, an RSV long terminal repeat (LTR) promoter, an simian virus 40 (SV40) promoter, a dihydrofolate reductase (DHFR) promoter, a beta-actin promoter, a phosphoglycerate kinase (PGK) promoter, and an elongation factor-1 alpha (EF-1 alpha) promoter. In some embodiments, the exogenous promoter is a CMV promoter. In some embodiments, the CMV promoter can comprise an enhancer region, a TATA box, and a transcription start point. In a preferred embodiment, the exogenous promoter comprises a CAG promoter system. In another preferred embodiment, the exogenous promoter comprises a SGE promoter system.

In some embodiments, the E3 region of the replication competent recombinant adenovirus described herein comprises a partial deletion compared to a wild type adenovirus of the same serotype. In some embodiments, the E3 region of the replication competent recombinant adenovirus comprises from about 0.1% to about 99.9% of a nucleic acid sequence of a gene or a transcription unit compared to a wild type adenovirus of the same serotype. In some embodiments, the partial deletion can be from about 0.1% to about 5%, from about 0.1% to about 10%, from about 0.1% to about 20%, from about 0.1% to about 30%, from about 0.1% to about 40%, from about 0.1% to about 50%, from about 0.1% to about 60%, from about 0.1% to about 70%, from about 0.1% to about 80%, from about 0.1% to about 90%, from about 0.1% to about 99.9%, from about 5% to about 10%, from about 5% to about 20%, from about 5% to about 30%, from about 5% to about 40%, from about 5% to about 50%, from about 5% to about 60%, from about 5% to about 70%, from about 5% to about 80%, from about 5% to about 90%, from about 5% to about 99.9%, from about 10% to about 20%, from about 10% to about 30%, from about 10% to about 40%, from about 10% to about 50%, from about 10% to about 60%, from about 10% to about 70%, from about 10% to about 80%, from about 10% to about 90%, from about 10% to about 99.9%, from about 20% to about 30%, from about 20% to about 40%, from about 20% to about 50%, from about 20% to about 60%, from about 20% to about 70%, from about 20% to about 80%, from about 20% to about 90%, from about 20% to about 99.9%, from about 30% to about 40%, from about 30% to about 50%, from about 30% to about 60%, from about 30% to about 70%, from about 30% to about 80%, from about 30% to about 90%, from about 30% to about 99.9%, from about 40% to about 50%, from about 40% to about 60%, from about 40% to about 70%, from about 40% to about 80%, from about 40% to about 90%, from about 40% to about 99.9%, from about 50% to about 60%, from about 50% to about 70%, from about 50% to about 80%, from about 50% to about 90%, from about 50% to about 99.9%, from about 60% to about 70%, from about 60% to about 80%, from about 60% to about 90%, from about 60% to about 99.9%, from about 70% to about 80%, from about 70% to about 90%, from about 70% to about 99.9%, from about 80% to about 90%, from about 80% to about 99.9%, or from about 90% to about 99.9% of a nucleic acid sequence of a gene or a transcription unit compared to a wild type adenovirus of the same serotype. In some embodiments, the partial deletion can be about 0.1%, about 5%, about 10%, about 20%, about 30%, about 40%, about 50%, about 60%, about 70%, about 80%, about 90%, or about 99.9% of a nucleic acid sequence of a gene or a transcription unit compared to a wild type adenovirus of the same serotype. In some embodiments, the partial deletion can be at least about 0.1%, about 1%, about 5%, about 10%, about 20%, about 30%, about 40%, about 50%, about 60%, about 70%, about 80%, about 90%, about 95%, or about 99.9% of a nucleic acid sequence of a gene or a transcription unit compared to a wild type adenovirus of the same serotype. In some embodiments, the partial deletion can be at most about 1%, about 5%, about 10%, about 20%, about 30%, about 40%, about 50%, about 60%, about 70%, about 80%, about 90%, or about 99.9% of a nucleic acid sequence of a gene or a transcription unit compared to a wild type adenovirus of the same serotype.

In some embodiments, the E3 region comprises a deletion from about 500 to 3,185 nucleotides. In some embodiments, the E3 region comprises a deletion from about 500 nucleotides to about 750 nucleotides, from about 500 nucleotides to about 1,000 nucleotides, from about 500 nucleotides to about 1,250 nucleotides, from about 500 nucleotides to about 1,500 nucleotides, from about 500 nucleotides to about 1,750 nucleotides, from about 500 nucleotides to about 2,000 nucleotides, from about 500 nucleotides to about 2,250 nucleotides, from about 500 nucleotides to about 2,500 nucleotides, from about 500 nucleotides to about 2,750 nucleotides, from about 500 nucleotides to about 3,000 nucleotides, from about 500 nucleotides to about 3,185 nucleotides, from about 750 nucleotides to about 1,000 nucleotides, from about 750 nucleotides to about 1,250 nucleotides, from about 750 nucleotides to about 1,500 nucleotides, from about 750 nucleotides to about 1,750 nucleotides, from about 750 nucleotides to about 2,000 nucleotides, from about 750 nucleotides to about 2,250 nucleotides, from about 750 nucleotides to about 2,500 nucleotides, from about 750 nucleotides to about 2,750 nucleotides, from about 750 nucleotides to about 3,000 nucleotides, from about 750 nucleotides to about 3,185 nucleotides, from about 1,000 nucleotides to about 1,250 nucleotides, from about 1,000 nucleotides to about 1,500 nucleotides, from about 1,000 nucleotides to about 1,750 nucleotides, from about 1,000 nucleotides to about 2,000 nucleotides, from about 1,000 nucleotides to about 2,250 nucleotides, from about 1,000 nucleotides to about 2,500 nucleotides, from about 1,000 nucleotides to about 2,750 nucleotides, from about 1,000 nucleotides to about 3,000 nucleotides, from about 1,000 nucleotides to about 3,185 nucleotides, from about 1,250 nucleotides to about 1,500 nucleotides, from about 1,250 nucleotides to about 1,750 nucleotides, from about 1,250 nucleotides to about 2,000 nucleotides, from about 1,250 nucleotides to about 2,250 nucleotides, from about 1,250 nucleotides to about 2,500 nucleotides, from about 1,250 nucleotides to about 2,750 nucleotides, from about 1,250 nucleotides to about 3,000 nucleotides, from about 1,250 nucleotides to about 3,185 nucleotides, from about 1,500 nucleotides to about 1,750 nucleotides, from about 1,500 nucleotides to about 2,000 nucleotides, from about 1,500 nucleotides to about 2,250 nucleotides, from about 1,500 nucleotides to about 2,500 nucleotides, from about 1,500 nucleotides to about 2,750 nucleotides, from about 1,500 nucleotides to about 3,000 nucleotides, from about 1,500 nucleotides to about 3,185 nucleotides, from about 1,750 nucleotides to about 2,000 nucleotides, from about 1,750 nucleotides to about 2,250 nucleotides, from about 1,750 nucleotides to about 2,500 nucleotides, from about 1,750 nucleotides to about 2,750 nucleotides, from about 1,750 nucleotides to about 3,000 nucleotides, from about 1,750 nucleotides to about 3,185 nucleotides, from about 2,000 nucleotides to about 2,250 nucleotides, from about 2,000 nucleotides to about 2,500 nucleotides, from about 2,000 nucleotides to about 2,750 nucleotides, from about 2,000 nucleotides to about 3,000 nucleotides, from about 2,000 nucleotides to about 3,185 nucleotides, from about 2,250 nucleotides to about 2,500 nucleotides, from about 2,250 nucleotides to about 2,750 nucleotides, from about 2,250 nucleotides to about 3,000 nucleotides, from about 2,250 nucleotides to about 3,185 nucleotides, from about 2,500 nucleotides to about 2,750 nucleotides, from about 2,500 nucleotides to about 3,000 nucleotides, from about 2,500 nucleotides to about 3,185 nucleotides, from about 2,750 nucleotides to about 3,000 nucleotides, from about 2,750 nucleotides to about 3,185 nucleotides, or from about 3,000 nucleotides to about 3,185 nucleotides. In some embodiments, the E3 region comprises a deletion of about 500 nucleotides, about 750 nucleotides, about 1,000 nucleotides, about 1,250 nucleotides, about 1,500 nucleotides, about 1,750 nucleotides, about 2,000 nucleotides, about 2,250 nucleotides, about 2,500 nucleotides, about 2,750 nucleotides, about 3,000 nucleotides, or about 3,185 nucleotides. In some embodiments, the E3 region comprises a deletion of at least about 500 nucleotides, about 750 nucleotides, about 1,000 nucleotides, about 1,250 nucleotides, about 1,500 nucleotides, about 1,750 nucleotides, about 2,000 nucleotides, about 2,250 nucleotides, about 2,500 nucleotides, about 2,750 nucleotides, or about 3,000 nucleotides. In some embodiments, the E3 region comprises a deletion of at most about 750 nucleotides, about 1,000 nucleotides, about 1,250 nucleotides, about 1,500 nucleotides, about 1,750 nucleotides, about 2,000 nucleotides, about 2,250 nucleotides, about 2,500 nucleotides, about 2,750 nucleotides, about 3,000 nucleotides, or about 3,185 nucleotides.

In some embodiments, the replication competent recombinant adenovirus described herein may comprise a modification in other regions of "E" genes or transcription units. In some embodiments, the adenovirus may comprise a modification in an E1 A, E1B, E2, or E4 gene.

In some embodiments, the E1 region of the replication competent recombinant adenovirus described herein comprises a partial deletion compared to a wild type adenovirus of the same serotype. In some embodiments, the partial deletion can be about 0.1% to about 5%, from about 0.1% to about 10%, from about 0.1% to about 20%, from about 0.1% to about 30%, from about 0.1% to about 40%, from about 0.1% to about 50%, from about 0.1% to about 60%, from about 0.1% to about 70%, from about 0.1% to about 80%, from about 0.1% to about 90%, from about 0.1% to about 99.9%, from about 5% to about 10%, from about 5% to about 20%, from about 5% to about 30%, from about 5% to about 40%, from about 5% to about 50%, from about 5% to about 60%, from about 5% to about 70%, from about 5% to about 80%, from about 5% to about 90%, from about 5% to about 99.9%, from about 10% to about 20%, from about 10% to about 30%, from about 10% to about 40%, from about 10% to about 50%, from about 10% to about 60%, from about 10% to about 70%, from about 10% to about 80%, from about 10% to about 90%, from about 10% to about 99.9%, from about 20% to about 30%, from about 20% to about 40%, from about 20% to about 50%, from about 20% to about 60%, from about 20% to about 70%, from about 20% to about 80%, from about 20% to about 90%, from about 20% to about 99.9%, from about 30% to about 40%, from about 30% to about 50%, from about 30% to about 60%, from about 30% to about 70%, from about 30% to about 80%, from about 30% to about 90%, from about 30% to about 99.9%, from about 40% to about 50%, from about 40% to about 60%, from about 40% to about 70%, from about 40% to about 80%, from about 40% to about 90%, from about 40% to about 99.9%, from about 50% to about 60%, from about 50% to about 70%, from about 50% to about 80%, from about 50% to about 90%, from about 50% to about 99.9%, from about 60% to about 70%, from about 60% to about 80%, from about 60% to about 90%, from about 60% to about 99.9%, from about 70% to about 80%, from about 70% to about 90%, from about 70% to about 99.9%, from about 80% to about 90%, from about 80% to about 99.9%, or from about 90% to about 99.9% of a nucleic acid sequence of a gene or a transcription unit compared to a wild type adenovirus of the same serotype. In some embodiments, the partial deletion can be about 0.1%, about 5%, about 10%, about 20%, about 30%, about 40%, about 50%, about 60%, about 70%, about 80%, about 90%, or about 99.9% of a nucleic acid sequence of a gene or a transcription unit compared to a wild type adenovirus of the same serotype. In some embodiments, the partial deletion can be at least about 0.1%, about 1%, about 5%, about 10%, about 20%, about 30%, about 40%, about 50%, about 60%, about 70%, about 80%, about 90%, about 95%, or about 99.9% of a nucleic acid sequence of a gene or a transcription unit compared to a wild type adenovirus of the same serotype. In some embodiments, the partial deletion can be at most about 1%, about 5%, about 10%, about 20%, about 30%, about 40%, about 50%, about 60%, about 70%, about 80%, about 90%, or about 99.9% of a nucleic acid sequence of a gene or a transcription unit compared to a wild type adenovirus of the same serotype.

A "partial deletion" as used herein may not be a full deletion of a gene or a transcription unit or a deletion of 100% of a nucleic acid sequence of a gene or a transcription unit compared to a wild type adenovirus of the same serotype. In a preferred embodiment, the E1 region of the replication competent recombinant adenovirus described herein does not comprise a complete deletion. In some embodiments, the E1 region of the replication competent recombinant adenovirus described herein does not contain an insertion of a heterologous nucleotide sequence. In some embodiments, the E1 region is derived from d11520 (Onyx-015) adenovirus. In some embodiments, the E1 region of the adenovirus comprises an E1B-55k deletion.

In some embodiments, the replication competent recombinant adenovirus described herein may comprise a polynucleotide sequence encoding a modified adenoviral fiber protein. The modification of the adenoviral fiber protein may enable targeting a host cell of interest. Without wishing to be bound by any particular theory, it is accepted that there are 57 human adenovirus serotypes and adenoviruses of different serotypes use different cellular receptors and entry mechanisms, and thus, have different tissue selectivity or tropism. The modification of the adenoviral fiber protein may enable alteration of tropism of an adenovirus of a certain serotype. Nicklin, et al., (2005) "The influence of adenovirus fiber structure and function on vector development for gene therapy" Mol. Ther. 12(3): 384-393; Shayakhmetov, et al., (2003) "The Interaction between the Fiber Knob Domain and the Cellular Attachment Receptor Determines the Intracellular Trafficking Route of Adenoviruses" J. Virol. 77(6): 3712-3723. Details of the modification of the adenoviral fiber protein is described in U.S. Pat. No. 7,094,398, the contents of which are incorporated herein by reference. In some embodiments, the replication competent recombinant adenovirus described herein may comprise a polynucleotide sequence encoding an adenoviral fiber protein of a different species or group, for example, group A, group B, group C, group D, group E, group F, or group G. In some embodiments, the replication competent recombinant adenovirus described herein may comprise a polynucleotide sequence encoding an adenoviral fiber protein of a different serotype. An adenoviral fiber protein may be of serotype 1 (Ad1), serotype 2 (Ad2), serotype 3 (Ad3), serotype 4 (Ad4), serotype 5 (Ad5), serotype 6 (Ad6), serotype 7 (Ad7), serotype 8 (Ad8), serotype 9 (Ad9), serotype 10 (Ad10), serotype 11 (Ad11), serotype 12 (Ad12), serotype 13 (Ad13), serotype 14 (Ad14), serotype 15 (Ad15), serotype 16 (Ad16), serotype 17 (Ad17), serotype 18 (Ad18), serotype 19 (Ad19), serotype 20 (Ad20), serotype 21 (Ad21), serotype 22 (Ad22), serotype 23 (Ad23), serotype 24 (Ad24), serotype 25 (Ad25), serotype 26 (Ad26), serotype 27 (Ad27), serotype 28 (Ad28), serotype 29 (Ad29), serotype 30 (Ad30), serotype 31 (Ad31), serotype 32 (Ad32), serotype 33 (Ad32), serotype 34 (Ad34), serotype 35 (Ad35), serotype 36 (Ad36), serotype 37 (Ad37), serotype 38 (Ad38), serotype 39 (Ad39), serotype 40 (Ad40), serotype 41 (Ad41), serotype 42 (Ad42), serotype 43 (Ad43), serotype 44 (Ad44), serotype 45 (Ad45), serotype 46 (Ad46), serotype 47 (Ad47), serotype 48 (Ad48), serotype 49 (Ad49), serotype 50 (Ad50), serotype 51 (Ad51), serotype 52 (Ad52), serotype 53 (Ad53), serotype 54 (Ad54), serotype 55 (Ad55), serotype 56 (Ad56), or serotype 57 (Ad57). In some embodiments, the replication competent recombinant adenovirus described herein may comprise a polynucleotide sequence encoding an adenoviral fiber protein of serotype 5 (Ad5). In some embodiments, the replication competent recombinant adenovirus described herein may comprise a polynucleotide sequence encoding an adenoviral fiber protein of serotype 35 (Ad35).

In some embodiments, the modified adenoviral fiber protein is of serotype 1 (Ad1), serotype 2 (Ad2), serotype 3 (Ad3), serotype 4 (Ad4), serotype 5 (Ad5), serotype 6 (Ad6), serotype 7 (Ad7), serotype 8 (Ad8), serotype 9 (Ad9), serotype 10 (Ad10), serotype 11 (Ad1 l), serotype 12 (Ad12), serotype 13 (Ad13), serotype 14 (Ad14), serotype 15 (Ad15), serotype 16 (Ad16), serotype 17 (Ad17), serotype 18 (Ad18), serotype 19 (Ad19), serotype 20 (Ad20), serotype 21 (Ad21), serotype 22 (Ad22), serotype 23 (Ad23), serotype 24 (Ad24), serotype 25 (Ad25), serotype 26 (Ad26), serotype 27 (Ad27), serotype 28 (Ad28), serotype 29 (Ad29), serotype 30 (Ad30), serotype 31 (Ad31), serotype 32 (Ad32), serotype 33 (Ad32), serotype 34 (Ad34), serotype 35 (Ad35), serotype 36 (Ad36), serotype 37 (Ad37), serotype 38 (Ad38), serotype 39 (Ad39), serotype 40 (Ad40), serotype 41 (Ad41), serotype 42 (Ad42), serotype 43 (Ad43), serotype 44 (Ad44), serotype 45 (Ad45), serotype 46 (Ad46), serotype 47 (Ad47), serotype 48 (Ad48), serotype 49 (Ad49), serotype 50 (Ad50), serotype 51 (Ad51), serotype 52 (Ad52), serotype 53 (Ad53), serotype 54 (Ad54), serotype 55 (Ad55), serotype 56 (Ad56), or serotype 57 (Ad57). In some embodiments, the modified adenoviral fiber protein is an Ad5 fiber tail protein. In a preferred embodiment, the modified adenoviral fiber protein is an Ad35 fiber tail protein.

In some embodiments, the replication competent recombinant adenovirus provided herein, may comprise a polynucleotide sequence encoding a chimeric fiber protein. The chimeric fiber protein may include a naturally occurring fiber protein with a portion or portions of the sequence modified to alter cell or tissue specificity. Modified fiber protein sequences may comprise fiber protein domains (the knob, shaft, and tail domains) from the same serotype or other serotypes, or from randomly selected peptides. A chimeric fiber protein can be composed of non-naturally occurring sequences entirely. In some embodiments, the modified fiber protein or the chimeric fiber protein may comprise a knob domain, a shaft domain, and a tail domain. In some embodiments, the modified fiber protein or the chimeric fiber protein may comprise a knob domain, a shaft domain, and a tail domain of different adenovirus serotypes. In some embodiments, the modified fiber protein or the chimeric fiber protein may comprise a knob domain of one serotype and a shaft domain and a tail domain of another serotype. In some embodiments, the modified fiber protein or the chimeric fiber protein may comprise a knob domain and a shaft domain of one serotype and a tail domain of another serotype. In some embodiments, the modified fiber protein or the chimeric fiber protein may comprise a knob domain of a first serotype (e.g., Ad1-Ad57), a shaft domain of a second serotype (e.g., Ad1-Ad57, except the two serotypes from which the knob and tail domains come from), and a tail domain of a third serotype (e.g., Ad1-Ad57, except the two serotypes from which the knob and shaft domains come from). For example, the modified fiber protein or the chimeric fiber protein may comprise the knob domain of Ad3, the shaft domain of Ad15, and the tail domain of Ad57. In some embodiments, the modified fiber protein comprises the knob domain of Ad35, the shaft domain of Ad35, and the tail domain of Ad5. In some embodiments, the modified fiber protein comprises a Ad35 tail. In some embodiments, a chimeric fiber protein comprises the knob domain of Ad35, the shaft domain of Ad35, and the tail domain of Ad5.

In some embodiments, the recombinant adenovirus provided herein comprises cis elements comprising inverted terminal repeats (ITRs) and a packaging signal (ψ) comprising A-repeats. In some embodiments, the recombinant adenovirus comprises an origin of replication sequence (ori). In some embodiments, the ori sequence can be from pMB1, pBR322, ColE1, R6K, pSC101, or F1 sequences. In a preferred embodiment, the ori sequence is pUC ori sequence. In some embodiments, the recombinant adenovirus comprises additional promoters (e.g., E1 A genes, MLP (Major Late Promoter), CMV (Cytomegalovirus), RSV (Rous Sarcoma Virus)) and elements such as one or more of enhancer. In some embodiments, the recombinant adenovirus comprises a sequence for internal ribosome entry site (IRES). In some embodiments, the recombinant adenovirus comprises a splice site. In some embodiments, the recombinant adenovirus comprises additional expression related sequences, e.g., a kozak sequence, polyadenylation (polyA) signal, termination signal. In some embodiments, the recombinant adenovirus comprises one or more multiple cloning site (MCS) comprising restriction enzyme sites. In some embodiments, the recombinant adenovirus comprises restriction enzyme sites. Non-limiting examples of restriction enzymes include AarI, AatII, Acc65I, AccI, AclI, AcuI, AfeI, AflII, AflIII, AgeI, AhdI, AjuI, AleI, AlfI, AloI, AlwNI, ApaI, ApaLI, ApoI, AscI, AseI, AsiSI, AvaI, AvrII, BaeGI, BaeI, BamHI, BanI, BanII, BarI, BbsI, BbvCI, BcgI, BciVI, BclI, BdaI, BfuAI, BglI, BglII, BlpI, Bme1580I, BmeT110I, BmgBI, BmrI, BmtI, BplI, BpmI, Bpul0I, BpuEI, BsaAI, BsaBI, BsaHI, BsaI, BsaWI, BsaXI, BseRI, BseYI, BsgI, BsiEI, BsiHKAI, BsiWI, BsmBI, BsmI, BsoBI, Bsp1286I, BspDI, BspEI, BspHI, BspMI, BspQI, BsrBI, BsrDI, BsrFI, BsrGI, BssHII, BssSI, BstAPI, BstBI, BstEII, BstXI, BstYI, BstZ17I, Bsu36I, BtgI, BtgZI, BtsI, ClaI, CspCI, DraI, DraIII, DrdI, EaeI, EagI, EarI, EciI, Eco53kI, Eco57MI, EcoNI, EcoO109I, EcoP15I, EcoRI, EcoRV, FalI, FseI, FspAI, FspI, HaeII, Hin4I, HincII, HindIII, HpaI, KasI, KflI, KpnI, MauBI, MfeI, MluI, MmeI, MreI, MscI, MslI, MspA1I, NaeI, NarI, NcoI, NdeI, NgoMIV, NheI, NmeAIII, NotI, NruI, NsiI, NspI, PacI, PaeR7I, PasI, PciI, PflFI, PflMI, PfoI, PluTI, PmeI, PmlI, PpiI, PpuMI, PshAI, PsiI, PspFI, PspOMI, PspXI, PstI, PvuI, PvuII, RsrII, SacI, SacII, SalI, SapI, SbfI, Scd, SexAI, SfcI, SfiI, SfoI, SgrAI, SmaI, SmlI, SnaBI, SpeI, SphI, SrfI, SspI, StuI, StyI, TaqII, TatI, TsoI, TspMI, TstI, Tth111I, XcmI, XhoI, XmaI, XmnI, ZraI. In preferred embodiments, the recombinant adenovirus comprises Pad, SwaI, AsiSI, MluI, RsrII, NotI, MluI, XhoI, EcoRI, BstBI, XbaI, SpeI, ClaI, BstBI, AflII, BstXi, AvrII, PmeI, NdeI, and BamHI restriction site. In some embodiments, the recombinant adenovirus comprises antibiotic resistance genes. Examples of antibiotic resistance genes include, but are not limited to, ampicillin, tetracycline, neomycin, zeocin, kanamycin, bleomycin, hygromycin, chloramphenicol, spectinomycin, streptomycin, carbenicillin, bleomycin, erythromycin, and polymyxin B. In some embodiments, the recombinant adenovirus comprises expression tags, e.g., His, Flag, CBP, GST, HA, HBH, MBP, Myc, S-tag, SUMO, TAP, TRX, or V5.

In certain embodiments, a recombinant adenovirus provided herein comprises a genetic element that allows tissue specific expression. For example, promoters or enhancers may be used depending on the level and tissue-specific expression desired. A promoter may be constitutive or inducible (e.g., the metallothionein promoter), depending on the pattern of expression desired. The promoter may be native or foreign and can be a natural or a synthetic sequence. By foreign, it is intended that the transcriptional initiation region is not found in the wild-type host into which the transcriptional initiation region is introduced. In particular embodiments, the promoter is chosen so that it will function in the target cell(s) or tissue(s) of interest, for example, a brain specific promoter, a hepatic specific promoter, a muscle specific promoter (including skeletal, cardiac, smooth, and/or diaphragm-specific), and any other cell type or tissue type specific promoters are contemplated. In some embodiments, the promoter is a mammalian specific promoter. Mammalian promoters are also preferred.

In some embodiments, the recombinant adenovirus provided herein comprises an early promotor. Examples of early promoters are well known in the art. In some embodiments, the early promotor can derive expression of a gene that is rapidly and transiently expressed in the absence of de novo synthesis. In some embodiments, the recombinant adenovirus provided herein comprises a strong or a weak promoter, each of which are well known in the art. In one embodiment, the strong or the weak promoter is defined by the relative frequency of transcription initiation (timers per minute) at the promoter. In another embodiment, the strong or the weak promoter is defined by the affinity to viral RNA polymerase.

In some embodiments, the recombinant adenovirus provided herein comprises a heterologous nucleotide sequence that are operatively associated with a human CMV major immediate-early promoter, a SV40 promoter, a β-actin promoter, an albumin promoter, an Elongation Factor 1-α (EF 1-α) promoter, a PγK promoter, a MFG promoter, or a RSV promoter. In some embodiments, the recombinant adenovirus comprises a sequence that controls the expression of a heterologous nucleotide sequence. In some embodiments, the expression control sequences comprises promoters derived from immunoglobin genes, adenovirus, bovine papilloma virus, or herpes virus. In some embodiments, the recombinant adenovirus can comprise any mammalian viral promoter. In some embodiments, driving expression of the heterologous nucleotide sequence with the CMV promoter may result in downregulation of expression of the heterologous nucleotide sequence in immunocompetent animals. Accordingly, in a preferred embodiment, the recombinant adenovirus described herein may comprise a heterologous nucleotide sequences operably associated with a modified CMV promoter that does not result in downregulation of expression of the heterologous nucleotide expression.

In some embodiments, the recombinant adenovirus described herein may comprise more than one heterologous nucleotide sequences. In some embodiments, more than one heterologous nucleotide sequences may be operatively associated with a single upstream promoter and one or more downstream internal ribosome entry site (IRES) sequences. In some embodiments, the IRES sequence may comprise a picornavirus EMC IRES sequence.

In some embodiments, the recombinant adenovirus described herein may comprise an exogenous initiation signal required for efficient transcription and translation of a heterologous nucleotide sequence in a target cell. In some embodiments, the exogenous initiation signal comprises an ATG initiation codon and adjacent sequences. In some embodiments, the exogenous initiation signal can be of a variety of origins. In one embodiment, the exogenous initiation signal is of natural origin. In another embodiment, the exogenous initiation signal is of synthetic origin.

In some aspects, provided herein, is a method of generating a replication competent recombinant adenovirus comprising a heterologous nucleotide sequence. In one aspect, the method comprises (a) cloning a heterologous nucleotide sequence into a shuttle vector; (b) digesting the shuttle vector in (a) with an I-CeuI restriction enzyme and a PI-SceI restriction enzyme to excise a fragment encompassing the heterologous nucleotide sequence; (c) digesting an adenovirus vector with the I-CeuI restriction enzyme and the PI-SceI restriction enzyme; (d) ligating the fragment encompassing the heterologous nucleotide sequence in (b) into the adenovirus vector in (c), thereby generating a recombinant adenoviral plasmid; (e) transfecting the recombinant adenoviral plasmid into a packaging cell; and (f) recovering the replication competent recombinant adenovirus from the packaging cell, wherein the adenovirus vector comprises an I-CeuI restriction site and a PI-SceI restriction site in an E3 region.

The practice of the present invention employs, unless otherwise indicated, conventional techniques of biology, including but not limited to molecular biology (including recombinant techniques), microbiology, cell biology, biochemistry and immunology, which are well within the purview of the skilled artisan. These techniques are applicable to the manufacture of the recombinant adenovirus of the present invention, and, as such, may be considered in making and practicing the invention. These techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). In addition, techniques for constructing, genetically manipulating, and propagating recombinant adenoviral vectors are disclosed in e.g., WO 2008/010864, U.S. Pat. Nos. 8,926,987, and 6,127,525, the contents of which are incorporated herein by reference.

For example, recombinant DNA technology can be employed to clone a heterologous nucleotide sequence into a shuttle vector. The heterologous nucleotide sequence can be generated with PCR based cloning to add restriction sites, which are compatible with the multiple cloning site (MCS) of a shuttle vector to which the heterologous nucleotide sequence will be inserted into (e.g., NheI, ApaI, XbaI, NotI, BstXI, KpnI, and AflII), to the ends of the heterologous nucleotide sequence. In some embodiments, the shuttle vector comprises NheI, ApaI, XbaI, NotI, BstXI, KpnI, or AflII restriction sites in MCS. In some embodiments, the heterologous nucleotide sequence can be generated with PCR based cloning to add NheI, ApaI, XbaI, NotI, BstXI, KpnI, or AflII restriction sites, or any combination thereof to the 5' and 3' ends of the heterologous nucleotide sequence. In some embodiments, the heterologous nucleotide sequence can be generated with PCR based cloning to add NheI and AflII restriction sites to 5' and 3' ends of the heterologous nucleotide sequence, respectively. In some embodiments, the heterologous nucleotide sequence can be generated with PCR based cloning to add ApaI and KpnI restriction sites to 5' and 3' ends of the heterologous nucleotide sequence, respectively. The heterologous nucleotide sequence and the shuttle vector can be subsequently digested with the same set of restriction enzymes that are added to the end of the heterologous nucleotide sequence and the heterologous nucleotide sequence is ligated into the shuttle vector to generate the shuttle vector containing the heterologous nucleotide sequence. The shuttle vector comprising the heterologous nucleotide sequence can be transformed or transfected into an appropriate host cell and cultivated under conditions suitable for expression. Next, the shuttle vector and the adenovirus vector containing I-CeuI and PI-SceI restriction sites in the E3 region with I-CeuI and PI-SceI restriction enzymes. The fragment encompassing the heterologous nucleotide sequence can be ligated into the adenovirus vector digested with the same restriction enzymes to generate a recombinant adenoviral plasmid. The recombinant adenoviral plasmid can be transformed or transfected into a packaging cell and the replication competent recombinant adenovirus can be harvested from the packaging cells and serial-passaged for higher yields. The adenoviral DNA can be isolated and tested to confirm the identity of the adenovirus is correct by PCR analysis, restriction digestion analysis, and sequencing analysis of the heterologous nucleotide sequence inserts and flanking regions.

In some embodiments, the shuttle vector is the pShuttle vector. In some embodiments, the heterologous nucleotide sequence of interest can be inserted into the MCS of pShuttle using one or more of any of the restriction sites available. In some embodiments, the heterologous nucleotide sequence of interest can be inserted into the MCS of pShuttle using any combination of the restriction sites. In some embodiments, the heterologous nucleotide sequence of interest may comprise a start codon for proper promoter driven expression in mammalian cells. In some embodiments, the heterologous nucleotide sequence of interest may be cDNA of a gene of interest. Once the heterologous nucleotide sequence of interest is cloned into pShuttle, the recombinant pShuttle vector can be digested with I-CeuI and PI-SceI to excise the mammalian expression cassette and the excised cassette can be inserted into the recombinant adenoviral vector or plasmid comprising I-CeuI and PI-SceI restriction sites in the E3 region. In some embodiments, the I-CeuI recognition sequence comprises 5'-TAACTATAACGGTCCTAAGGTAGCGA-3' (SEQ ID NO: 1). In some embodiments, the PI-Sce I recognition sequence comprises 5'-ATCTATGTCGGGTGCGGAGAAAGAGGTAATGAAATGGCA-3' (SEQ ID NO: 2).

Heterologous Nucleotide Sequence

In one aspect, the replication competent recombinant adenovirus described herein comprises one or more heterologous nucleotide sequence. in some embodiments, the replication competent recombinant adenovirus comprises one, two, three, or more heterologous nucleotide sequences. The heterologous nucleotide sequences may encode mRNAs or polypeptides. In some embodiments, the heterologous nucleotide sequence may be located between the I-CeuI restriction site and the PI-SceI restriction site in the E3 region. In some embodiments, the heterologous nucleotide sequence comprises a gene. In some embodiments, the heterologous nucleotide sequence comprises a gene that encodes a protein. In some embodiments, the heterologous nucleotide sequence comprises one or more open reading frames (ORFs).

A heterologous nucleotide of a recombinant adenovirus of the present disclosure can include any and all genes or polynucleotide of interest. In some embodiments, a heterologous nucleotide sequence encodes a therapeutic polypeptide for gene therapy. For example, the heterologous nucleotide sequence may encode a therapeutic polypeptide or protein for: cystic fibrosis transmembrane regulator protein (CFTR), dystrophin (including the protein product of dystrophin mini-genes, see, e.g, Vincent et al., 1993), utrophin (Tinsley et al., 1996), dotting factors (e.g., Factor XII, Factor IX, Factor X, etc.), erythropoietin, the LDL receptor, lipoprotein lipase, ornithine transcarbamylase, β-globin, α-globin, spectrin, α-antitrypsin, adenosine deaminase, hypoxanthine guanine phosphoribosyl transferase, β-glucocerebrosidase, sphingomyelinase, lysosomal hexosaminidase, branched-chain keto acid dehydrogenase, Angiotensin-converting enzyme (ACE), Adenylyl Cyclase Type 5 (AC5), AMPK, Angiopoietin-like 4 (ANGPTL4), Angiotensin II receptor type 1 (Agtr1a), Apolipoprotein A-1, APOE, ARID1A, Activating transcription factor 4 (ATF4), Atoh1, Azot, BCAT-1, β2 microglobulin (B2M), BubR1, C-Myc, C1Q, Catalase, CLK1, CRTC1, Cyclin A2, FGF21, FKBP1b, Follistatin, FOXO3, FOXN1, GDF11, GHK, Glycine N-methyltransferase (Gnmt), Growth hormone/growth hormone receptor/insulin-like growth factor/insulin receptor, Histone deacetylase 2 (HDAC2), Heat shock proteins, Hepatic transcription factors, Hepatocyte growth factor (HGF), INDY, interleukin-21 (IL-21), KLF4, Klotho, Lamins including Lamin A, Lamin B, and Lamin C, LAMP2A, leukemia inhibitory factor (LIF), Lin28a, LOS1, miR-195, mitochondrial Complex I, mechanistic target of rapamycin (mTOR), Myostatin, NAD-dependent methylenetetrahydrofolate dehydrogenase-methenyltetrahydrofolate cyclohydrolase (NMDMC), NF-κB, NRF2/SKN-1, Oct4, P16, P21, P53, PCSK9, Parkin, Per2, PGC-1, PHD1, PEPCK, PIM1, plasminogen activator inhibitor-1 (PAI-1), Pregnancy-associated plasma protein-A (PAPP-A), Phosphatase and tensin homolog (PTEN), RbAp48, Reticulon 4 receptor (RTN4R), Rpd3, SERCA2a/SUMO-1, Sirtuins, Telomerase, TGF-β1, Transcription factor EB (TFEB), Troponin C, TRPV1, uncoupling proteins (UCP), urokinase, (uPA), VEGF, Gata4, Mef2c, Tbx5, and adenosine deaminase (ADA).

In some embodiments, a heterologous nucleotide sequence encodes a hormone. Non-limiting examples of hormones include amino acid derived hormones such as epinephrine, melatonin, norepinephrine, triiodothyronine, thyroxine, and dopamine; eicosanoid such as prostaglandins, leukotrienes, prostacyclin, and thromboxane; peptide such as amylin, anti-mullerian hormone, adiponectin, adrenocorticotropic hormone, angiotensinogen, angiotensin, antidiuretic hormone, atrial-natriuretic peptide, brain natriuretic peptide, calcitonin, cholecystokinin, corticotrophin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, insulin-like growth factor, leptin, lipotropin, luteinizing hormone, melanocyte stimulating hormone, motilin, orexin, osteocalcin, oxytocin, pancreatic polypeptide, parathyroid hormone, pituitary adenylate cyclase-activating peptide, prolactin, prolactin-releasing hormone, relaxin, renin, secretin, somatostatin, thrombopoietin, thyroid-stimulating hormone, thyrotropin-releasing hormone, vasoactive intestinal peptide, guanylin, and uroguanylin; steroid such as androgen, dehydroepiandrosterone, androstenedione, dihydrotestosterone, aldosterone, estradiol, estrone, estriol, cortisol, progesterone, calcitriol (1,25-dihydroxyvitamin D3), and calcidiol (25-hydroxyvitamin D3).

In some embodiments, a heterologous nucleotide sequence encodes a growth factor. Non-limiting examples of growth factors include adrenomedullin (AM), angiopoietin (Ang), autocrine motility factor, bone morphogenetic proteins (BMPs), ciliary neurotrophic factor (CNTF), leukemia inhibitory factor (LIF), interleukin-6 (IL-6), macrophage colony-stimulating factor (M-CSF), granulocyte colony-stimulating factor (G-CSF), granulocyte macrophage colony-stimulating factor (GM-CSF), epidermal growth factor (EGF), ephrins A1-A5, ephrins B1-B3, erythropoietin (EPO), fibroblast growth factors 1-23 (FGF1-23), foetal bovine somatotrophin (FBS), glial cell line-derived neurotrophic factor (GDNF), neurturin, persephin, artemin, growth differentiation factor-9 (GDF9), hepatocyte growth factor (HGF), hepatoma-derived growth factor (HDGF), insulin, inulin-like growth factors 1-2 (IGF1 and IGF2), interleukins 1-7 (IL-1, IL-2, IL-3, IL-4, IL-5, IL-6, and IL-7), keratinocyte growth factor (KGF), migration-stimulating factor (MSF), macrophage-stimulating protein (MSP), myostatin (GDF-8), neuregulins 1-4 (NRG1-4), brain-derived neurotrophic factor (BDNF), nerve growth factor (NGF), neurotrophin-3 (NT-3), neurotrophin-4 (NT-4), placental growth factor (PGF), platelet-derived growth factor (PDGF), renalase (RNLS), T-cell growth factor (TCGF), thrombopoietin (TPO), transforming growth factor-alpha (TGF-α), transforming growth factor-beta (TGF-β), tumor necrosis factor-alpha (TNF-α), vascular endothelial growth factor (VEGF), and genes involved in WNT signaling pathway.

In some embodiments, a heterologous nucleotide sequence encodes an immune-effector or immune-modulatory polypeptide or protein. In some embodiments, a heterologous nucleotide sequence encodes a checkpoint inhibitor. Non-limiting examples of checkpoint inhibitor targets include cytotoxic T-lymphocyte-associated protein 4 (CTLA4), programmed cell death 1 (PD-1), and PD-1 ligand 1 (PD-L1). Non-limiting examples of checkpoint inhibitors include Ipilimumab, Nivolumab, Pembrolizumab, Atezolizumab, Avelumab, Durvalumab, and Cemiplimab. In some embodiments, the heterologous polynucleotide sequence comprises an angiogenic gene. In some embodiments, a heterologous nucleotide sequence encodes cytokines such as IL-1β, IL-1Ra, IL-2, IL-6, IL-10, IL-12, IL-17A, IL-23, TGF-β, TNF-α, GM-CSF; chemokines such as CCL1, CCL2, CCL3, CCL4, CCL5, CCL6, CCL7, CCL8, CCL9, CCL10, CCL11, CCL12, CCL13, CCL14, CCL15, CCL16, CCL17, CCL18, CCL19, CCL20, CCL21, CCL22, CCL23, CCL24, CCL25, CCL26, CCL27, CCL28, CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, CXCL17, XCL1, XCL2, and CX3CL1; co-stimulatory molecules such as CD28, ICOS, CD40, CD40L, B7-1, B7-2, B7-DC, B7-H1, B7-H2, B7-H3, B7-H4, B7-H5, B7-H6, and B7-H7. In some embodiments, the heterologous polynucleotide comprises a IL-2 gene. In some embodiments, a heterologous nucleotide sequence encodes suicide genes, hymidine kinase, cytosine deaminase, diphtheria toxin, and tumor necrosis factor. In some embodiments, a heterologous nucleotide sequence encodes proteins conferring resistance to a drug used in cancer therapy. In some embodiments, the heterologous polynucleotide comprises enzymes, blood derivatives, hormones, lymphokines, interleukins, interferons, TNF, growth factors, neurotransmitters or their precursors, synthetic enzymes, trophic factors, BDNF, CNTF, NGF, IGF, GMF, aFGF, bFGF, NT3, NTS, apolipoproteins ApoAI, ApoAIV, ApoE, dystrophin, minidystrophin, tumor suppressor genes such as p53, Rb, Rap1A, DCC, k-rev, genes of coagulation factors such as Factors VII, VIII, IX, and suicide genes. In some embodiments, the heterologous polynucleotide comprises a dickkopf WNT signaling pathway inhibitor 3 (DKK3, or REIC gene). In some embodiments, the heterologous polynucleotide comprises, an antisense gene or sequence that can control the expression of genes.

In some embodiments, a heterologous nucleotide sequence encodes a antigen or antigenic polypeptide or a portion thereof. In some embodiments, the heterologous nucleotide sequence encodes one or more of an epitope of interest from a pathogen, e.g., an epitope, antigen, or gene product which modifies allergic response, an epitope antigen or gene product which modifies physiological function, influenza hemagglutinin, influenza nuclear protein, influenza M2, tetanus toxin C-fragment, anthrax protective antigen, anthrax lethal factor, rabies glycoprotein, HBV surface antigen, HIV gpl20, HIV gp160, human carcinoembryonic antigen, malaria CSP, malaria SSP, malaria MSP, malaria pfg, Epstein Barr virus, HIV virus, hepatitis B virus, pseudorabies virus, tumor-specific virus, and *Mycobacterium tuberculosis* HSP; and/or a therapeutic or an immunomodulatory gene, a co-stimulatory gene and/or a cytokine gene. In some embodiments, a recombinant adenovirus vector provided herein is used to immunize or inoculate a subject.

In some embodiments, the heterologous nucleotide sequence encodes one or more tumor antigens. In some embodiments, the heterologous nucleotide sequence encodes one or more of an epitope of interest of a tumor antigen. In some embodiments, the heterologous nucleotide sequence encodes on or more tumor repressors. In some embodiments, the heterologous nucleotide sequence encodes one or more polypeptides selected from MAGE-1, MAGE-2, MAGE-3, CEA, Tyrosinase, midkine, BAGE, CASP-8, β-catenin, CA-125, CDK-1, ESO-1, gp75, gplOO, MART-1, MUC-1, MUM-1, p53, PAP, PSA, PSMA, ras, trp-1, HER-2, TRP-1, TRP-2, IL13Ralpha, IL13Ralpha2, AIM-2, AIM-3, NY-ESO-1, C9orfll2, SART1, SART2, SART3, BRAP, RTN4, GLEA2, T KS2, KIAA0376, ING4, HSPH1, C13orf24, REIC, RBPSUH, C6orfl53, KTR, NSEP1, U2AF1L, CY L2, TPR, SOX2, GOLGA, BMI1, COX-2, EGFRvIII, EZH2, LICAM, Livin, MRP-3, Nestin, OLIG2, ART1, ART4, B-cyclin, Glil, Cav-1, cathepsin B, CD74, E-cadherin, EphA2/Eck, GAGE-1, Ganglioside/GD2, GnT-V, 131,6-N, Ki67, Ku70/80, PROX1, PSCA, SOX10, SOX11, Survivin, UPAR, Mesothelin, and WT-1, or an epitope thereof (additional protooncogenes: RET, ERBB2 or HER2, PDGF-Rβ, SRC, PRAD1/cyclin D1, C-Myc, BCL2, ABL, MDM2, p110α, B-RAF, IDH1, IDH2, JAK2, KIT, MET, FLT-3, VEGF, VEGFR, SKY, etc.) In some embodiments, the heterologous nucleotide sequence encodes a polypeptide selected from p53, RB, BCL2, SWI/SNF, RAP1A, DCC, K-REV, WT1, TBR-11, INK4A/ARF, SMAD2, SMAD3, SMAD4/DPC4, E-CADHERIN, APC, VHL, PTEN/MMAC1, NF1, NF2, BRCA1, BRCA2, MSH2, MLH1, PMS1, PMS2, REIC, SDHB, SDHD, and GP43/Merlin.

Sequences of the heterologous polynucleotides may comprise a gene of an organism, for example, an animal gene, a vertebrate gene, a mammalian gene, a mouse gene, a rat gene, a rabbit gene, a non-human primate gene, or a human gene. In some embodiments, the heterologous polynucleotide sequence is codon-optimized for expression.

In some embodiments, the heterologous nucleotide sequence is operably associated with a expression control sequence, e.g., a promoter. In some embodiments, the promoter is an exogenous promoter. In some embodiments, the exogenous promoter is operably linked to the E3 region, the E1 region, or the heterologous nucleotide sequence of a recombinant adenovirus vector. In some embodiments, the exogenous promoter is operably linked to the E3 region. In some embodiments, the exogenous promoter is operably linked to the E1 region. In some embodiments, the exogenous promoter is operably linked to a heterologous nucleotide sequence. In some embodiments, the exogenous promoter can be an inducible promoter, a cell specific promoter, a developmental specific promoter, or a tissue specific promoter. In some embodiments, the exogenous promoter is a tissue specific promoter. Examples of tissue specific promoters include, but are not limited to, a FABP promoter, an Lck promoter, a CamKII promoter, a CD19 promoter, a Keratin promoter, an Albumin promoter, an aP2 promoter, an insulin promoter, an MCK promoter, a MyHC promoter, a WAP promoter, or a Col2A promoter. In some embodiments, the exogenous promoter may be selected from the group consisting of a CMV promoter, an RSV LTR promoter, an SV40 promoter, a DHFR promoter, a beta-actin promoter, a PGK promoter, and an EF-1 alpha promoter. In some embodiments, the exogenous promoter is a CMV promoter. In some embodiments, the CMV promoter can comprise an enhancer region, a TATA box, and a transcription start point. In a preferred embodiment, the exogenous promoter comprises a CAG promoter system. In some embodiments, the exogenous promoter comprises a SGE promoter system. In a preferred embodiment, the heterologous nucleotide sequence comprises a REIC (reduced expression in immortalized cells) sequence.

Kits and Host Cells

The replication competent recombinant adenovirus described herein can be provided in a kit with a shuttle vector to insert a gene of interest to produce an oncolytic adenovirus, the kit may include the replication competent recombinant adenovirus and the shuttle vector separately in different containers, instructions, and other necessary components. The kit can also include a carrier, a package, or a container that is compartmentalized to receive one or more containers such as vials, tubes, and the like, each of the container(s) comprising one of the separate elements, such as the replication competent recombinant adenovirus and the shuttle vector to be used in a method described herein. Suitable containers include, but are not limited to, bottles, vials, syringes, and test tubes. The containers can be formed from a variety of materials such as glass or plastic.

The kit can contain a vector map, a host cell, a cultivation medium for cultivation in the host cell, a selection medium for selecting and cultivating a transfected host cell. The kit can additionally contain labels and/or package inserts listing contents and/or instructions for use. The kit can be provided as, or contain, a suitable container for shipping. The shipping container can be an insulated container. The shipping container can be self-addressed to a collection agent (e.g., laboratory, medical center, genetic testing company, etc.). The kit can be provided for use by a medical professional or a laboratory personnel. The kit can be provided directly to a medical professional or a laboratory personnel.

In some aspects, provided herein, is a kit comprising a shuttle vector and the replication competent recombinant adenovirus described herein to produce an oncolytic adenovirus. In some embodiments, the shuttle vector is a pShuttle vector. The kit can be provided herein for use with one or more methods described herein for expressing a gene in a host cell. The kit can contain one or more replication competent recombinant adenovirus and one or more shuttle vector. The kit provided herein can contain additional packaging materials. Examples of packaging materials include, but are not limited to, blister packs, bottles, tubes, bags, containers, bottles, and any packaging material suitable for the oncolytic adenovirus product.

In some aspects, provided herein, is a host cell comprising the replication competent recombinant adenovirus described herein. Non-limiting examples of host cells include eukaryotic cells such as animal cells including cells of bats, squirrels, horses, cattle, pigs, sheep, goats, dogs, sea lions, birds, monkeys, and humans. In some embodiments, the host cell is a human cell. In some embodiments, the host cell is a tumor cell. In some embodiments, a tumor cell can be isolated from a patient sample, for example, a tissue biopsy, pleural effusion, or blood sample, mixed with immune cells (e.g., T cells), and cultured in a medium to which the replication competent recombinant adenovirus is added. In some embodiments, a tumor cell may be of a cancer listed herein. In some embodiments, the replication competent recombinant adenovirus described herein increases, promotes, and/or enhances anti-tumor activity. In some embodiments, the replication competent recombinant adenovirus described herein inhibits tumor cell growth. In some embodiments, the replication competent recombinant adenovirus described herein activates tumor cell killing. In some embodiments, the replication competent recombinant adenovirus described herein initiates tumor cell killing.

In some embodiments, the host cell can be a cell for production or packaging of the adenovirus, e.g., prokaryotic cell lines for adenovirus packaging. In some embodiments, the host cells can be bacterial cells, such as *Escherichia coli, Bacillus subtilis, Salmonella typhimurium, Rhizobium meliloti, Agrobacterium tumefaciens, Enterococcus faecium*, and various species within the genera *Pseudomonas* including *Pseudomonas putida, Pseudomonas aeruginosa, Streptomyces* including *Streptomyces pristinaespiralis, Staphylococcus* including *Staphylococcus aureus*, and *Clostridium*. In some embodiments, the host cell can be for expression, e.g., eukaryotic cells such as mammalian cells, non-human primate cells, or yeast cells. In some embodiments, the host cells can be fungal cells, such as yeast; insect cells such as *Drosophila* and Sf9; animal cells such as COS-7 lines of monkey kidney fibroblasts, described by Gluzman, Cell 23:175 (1981), and other cell lines capable of expressing a compatible adenovirus vector, for example, the C127, 3T3, CHO, HeLa, and BHK cell lines, or Bowes melanoma; plant cells, etc. The selection of an appropriate host is deemed to be within the scope of those skilled in the art from the teachings herein.

In some embodiments, the host cell can be the effect/effector cells or target cells for therapeutic use. Examples include but are not limited to epithelial cells; retinal cells; muscle cells including skeletal muscle cells, cardiac muscle cells, and smooth muscle cells; cartilage cells including chondrocytes; hepatic cells; endothelial cells; bone cells including osteoblasts, osteoclasts, osteocytes, and lining cells; nerve cells including neurons and neuroglial cells; blood cells including granulocytes, agranulocytes, neutrophils, eosinophils, basophils, lymphocytes, erythrocytes, platelets; stem cells including adult stem cells and embryonic stem cells; adipose cells including white adipocytes and brown adipocytes; skin cells including keratinocytes, melanocytes, Merkel cells, and Langerhans cells; sex cells including spermatozoa and ova; renal cells; cardiac cells; pancreatic cells; intestinal cells; lung cells; and gastric cells.

In some embodiments, the host cell is an engineered host cell. The engineered host cell can be cultured in conventional nutrient media modified as appropriate for activating promoters, selecting transformants or amplifying the polynucleotides. The culture conditions, such as temperature, pH and the like, are those previously used with the host cell selected for expression, and will be apparent to the ordinarily skilled artisan.

In some aspects, provided herein, is a method for expressing a gene in a host cell, the method comprising contacting the host cell with an effective amount of the adenovirus described herein, thereby expressing the gene in the host cell. The term "effective amount," as used herein, refers to an amount of a biologically active agent that is sufficient to elicit a desired biological response. The effective amount of an active agent(s) used to practice the present invention for expressing the gene of interest varies depending upon the host cell type, method of contacting or delivery of the recombinant adenovirus, etc.

Pharmaceutical Composition and Methods of Treatment

In some aspects, provided herein, is a pharmaceutical composition comprising the replication competent recombinant adenovirus described herein and a pharmaceutically acceptable carrier. The replication competent recombinant adenovirus described herein can be formulated into pharmaceutical compositions. Pharmaceutical compositions are formulated in a conventional manner using one or more pharmaceutically acceptable inactive ingredients that facilitate processing of the active compounds into preparations that can be used pharmaceutically. Suitable formulations for use in the present invention and methods of delivery are generally well known in the art. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition can be a mixture of an adenovirus described herein with one or more of other chemical components (i.e., pharmaceutically acceptable ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the adenovirus to an organism or a subject in need thereof.

The pharmaceutical compositions of the present invention can be administered to a subject using any suitable methods known in the art. The pharmaceutical compositions described herein can be administered to the subject in a variety of ways, including parenterally, intravenously, intradermally, intramuscularly, colonically, rectally, or intraperitoneally. In some embodiments, the pharmaceutical compositions can be administered by intraperitoneal injection, intramuscular injection, subcutaneous injection, or intravenous injection of the subject. In some embodiments, the pharmaceutical compositions can be administered parenterally, intravenously, intramuscularly, or orally.

For administration by inhalation, the adenovirus described herein can be formulated for use as an aerosol, a mist, or a powder. For buccal or sublingual administration, the pharmaceutical compositions may be formulated in the form of tablets, lozenges, or gels formulated in a conventional manner. In some embodiments, the adenovirus described herein can be prepared as transdermal dosage forms. In some embodiments, the adenovirus described herein can be formulated into a pharmaceutical composition suitable for intramuscular, subcutaneous, or intravenous injection. In some embodiments, the adenovirus described herein can be administered topically and can be formulated into a variety of topically administrable compositions, such as solutions, suspensions, lotions, gels, pastes, medicated sticks, balms, creams, or ointments. In some embodiments, the adenovirus described herein can be formulated in rectal compositions such as enemas, rectal gels, rectal foams, rectal aerosols, suppositories, jelly suppositories, or retention enemas. In some embodiments, the adenovirus described herein can be formulated for oral administration such as a tablet, a capsule, or liquid in the form of aqueous suspensions or solutions selected from the group including, but not limited to, aqueous oral dispersions, emulsions, solutions, elixirs, gels, and syrups.

In some embodiments, the pharmaceutical composition comprising the replication competent recombinant adenovirus further comprises a therapeutic agent. The additional therapeutic agent may modulate different aspects of the disease, disorder, or condition being treated and provide a greater overall benefit than administration of either the replication competent recombinant adenovirus or the therapeutic agent alone. Therapeutic agents include, but are not limited to, a chemotherapeutic agent, a radiotherapeutic agent, a hormonal therapeutic agent, and/or an immunotherapeutic agent. In some embodiments, the therapeutic agent may be a radiotherapeutic agent. In some embodiments, the therapeutic agent may be a hormonal therapeutic agent. In some embodiments, the therapeutic agent may be an immunotherapeutic agent. In a preferred embodiment, the therapeutic agent is a chemotherapeutic agent. Preparation and dosing schedules for chemotherapeutic agents can be used according to manufacturers' instructions or as determined empirically by a skilled practitioner. Preparation and dosing schedules for such chemotherapy are also described in The Chemotherapy Source Book, 4th Edition, 2008, M. C. Perry, Editor, Lippincott, Williams & Wilkins, Philadelphia, PA.

A list of non-limiting examples of chemotherapeutic agents includes anti-tubulin agents, auristatins, DNA minor groove binders, DNA replication inhibitors, alkylating agents (e.g., temozolomide, cyclophosphamide, ifosfamide, chlorambucil, busulfan, melphalan, mechlorethamine, uramustine, thiotepa, nitrosoureas, etc.), anthracyclines, antifolates, anti-metabolites (e.g., 5-fluorouracil, azathioprine, methotrexate, leucovorin, capecitabine, cytarabine, floxuridine, fludarabine, gemcitabine, pemetrexed, raltitrexed, tegafur, cytosine arabinoside, thioguanine, 5-azacytidine, 6 mercaptopurine, 6-thioguanine, pentostatin, cladribine, etc.), chemotherapy sensitizers, duocarmycins, etoposides, fluorinated pyrimidines, ionophores, lexitropsins, platinols, plant alkaloids (e.g., vincristine, vinblastine, vinorelbine, vindesine, podophyllotoxin, paclitaxel, docetaxel, etc.), puromycins, radiation sensitizers, topoisomerase inhibitors (e.g., irinotecan, topotecan, amsacrine, etoposide (VP16), etoposide phosphate, teniposide (VM-26), doxorubicin HCl, daunorubicin citrate, mitoxantrone HCl, actinomycin D, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g., cisplatin, oxaloplatin, carboplatin, etc.), EGFR inhibitors (e.g., gefitinib, erlotinib, etc.), PARP inhibitors (e.g., olaparib, rucaparib, niraparib, talazoparib, etc.), steroids, taxanes, vinca alkaloids, and the like.

Alkylating agents include, but are not limited to, thiotepa and cyclosphosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); taxoids, e.g., paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin.

In some embodiments, the chemotherapeutic agent may comprise an alkylating agent such as nitrogen mustard (e.g., mechlorethamine (nitrogen mustard), chlorambucil, cyclophosphamide (Cytoxan®), ifosfamide, and melphalan); nitrosourea (e.g., N-Nitroso-N-methylurea, streptozocin, carmustine (BCNU), lomustine, and semustine); alkyl sulfonate (e.g., busulfan); tetrazine (e.g., dacarbazine (DTIC), mitozolomide and temozolomide (Temodar®)); aziridine (e.g., thiotepa, mytomycin and diaziquone); and a platinum drug (e.g., cisplatin, carboplatin, and oxaliplatin); a non-classical alkylating agent such as procarbazine and altretamine (hexamethylmelamine); anti-metabolite agents such as 5-fluorouracil (5-FU), 6-mercaptopurine (6-MP), capecitabine (Xeloda®), cladribine, clofarabine, cytarabine (Ara-C®), decitabine, floxuridine, fludarabine, nelarabine, gemcitabine (Gemzar®), hydroxyurea, methotrexate, pemetrexed (Alimta®), pentostatin, thioguanine, Vidaza; an anti-microtubule agent such as vinca alkaloid (e.g., vincristine, vinblastine, vinorelbine, vindesine and vinflunine); taxane (e.g., paclitaxel (Taxol®), docetaxel (Taxotere®)); podophyllotoxin (e.g., etoposide and teniposide); epothilone (e.g., ixabepilone (Ixempra®)); estramustine (Emcyt®); an anti-tumor antibiotic such as anthracycline (e.g., daunorubicin, doxorubicin (Adriamycin®, epirubicin, idarubicin); actinomycin-D; and bleomycin; a topoisomerase I inhibitor such as topotecan and irinotecan (CPT-11); a topoisomerase II inhibitor such as etoposide (VP-16), teniposide, mitoxantrone, novobiocin, merbarone and aclarubicin; corticosteroid such as prednisone, methylprednisolone (Solumedrol®), and dexamethasone (Decadron®); L-asparaginase; bortezomib (Velcade®); an immunotherapeutic agent such as rituximab (Rituxan®), alemtuzumab (Campath®), thalidomide, lenalidomide (Revlimid®), BCG, interleukin-2, interferon-alfa and a cancer vaccine such as Provenge®; a hormone therapeutic agent such as fulvestrant (Faslodex®), tamoxifen, toremifene (Fareston®), anastrozole (Arimidex®), exemestan (Aromasin®), letrozole (Femara®), megestrol acetate (Megace®), estrogens, bicalutamide (Casodex®), flutamide (Eulexin®), nilutamide (Nilandron®), leuprolide (Lupron®) and goserelin (Zoladex®); a differentiating agent such as retinoids, tretinoin (ATRA or Atralin®), bexarotene (Targretin®) and arsenic trioxide (Arsenox®); and a targeted therapeutic agent such as imatinib (Gleevec®), gefitinib (Iressa®) and sunitinib (Sutent®). In some embodiments, the chemotherapeutic agent is a cocktail of chemotherapeutic agents. Examples of a cocktail therapy includes, but is not limited to, CHOP/R-CHOP (rituxan, cyclophosphamide, hydroxydoxorubicin, vincristine, and prednisone), EPOCH (etoposide, prednisone, vincristine, cyclophosphamide, hydroxydoxorubicin), Hyper-CVAD (cyclophosphamide, vincristine, hydroxydoxorubicin, dexamethasone), FOLFOX (fluorouracil (5-FU), leucovorin, oxaliplatin), ICE (ifosfamide, carboplatin, etoposide), DHAP (high-dose cytarabine [ara-C], dexamethasone, cisplatin), ESHAP (etoposide, methylprednisolone, cytarabine [ara-C], cisplatin) and CMF (cyclophosphamide, methotrexate, flouuracil).

In some embodiments, the replication competent recombinant adenovirus described herein can be typically administered at a much lower dose than would be needed to achieve equivalent expression levels of the encoded transgene by a replication defective recombinant adenovirus in vivo. Replication competent adenovirus vectors can be administered at a range of dosages, which are described in, for example, U.S. Pat. No. 4,920,209; Smith et al., J. Infec. Dis. 122:239-248, 1970; Top et al., J. Infect. Dis. 124:155-160, 1971; Takafuji et al., J. Infec. Dis. 140:48-53, 1979; Tacket et al., Vaccine 10:673-676, 1992.

In some aspects, provided herein, is a method of treating a proliferative disorder in a subject in need thereof, comprising administering the adenovirus described herein, or the pharmaceutical composition described herein to the subject. In some embodiments, the proliferative disorder is a cancer. In some embodiments, the cancer is a cancer selected from the group consisting of colorectal cancer, renal cancer, pancreatic cancer, lung cancer, ovarian cancer, liver cancer, breast cancer, kidney cancer, prostate cancer, gastrointestinal cancer, melanoma, cervical cancer, neuroendocrine cancer, bladder cancer, uterine cancer, glioblastoma, esophageal cancer, thyroid cancer, glioma, leukemia, lymphoma, carcinoma, squamous carcinoma, adenocarcinoma, sarcoma, endometrial cancer, fallopian tube cancer, primary peritoneal cancer, squamous cell carcinoma of the anogenital region, colon cancer, stomach cancer, gall bladder cancer, laryngeal cancer, salivary gland cancer, mesothelioma, sarcoma, hematological cancer, neuroma, skin cancer, and head and neck cancer. In certain embodiments, the cancer is pancreatic cancer. In certain embodiments, the cancer is ovarian cancer. In certain embodiments, the cancer is colorectal cancer. In certain embodiments, the cancer is breast cancer. In certain embodiments, the cancer is prostate cancer. In certain embodiments, the cancer is lung cancer. In certain embodiments, the cancer is non-small cell lung cancer. In certain embodiments, the cancer is uterine cancer. In certain embodiments, the cancer is liver cancer. In certain embodiments, the cancer is melanoma. In some embodiments, the cancer is a solid cancer. In some embodiments, the cancer comprises a solid tumor.

In some embodiments, administering the adenovirus or the pharmaceutical composition described herein to the subject is in combination with one or more therapies selected from the group consisting of surgery, radiation, chemotherapy, immunotherapy, and hormone therapy. In some embodiments, administering the adenovirus or the pharmaceutical composition described herein to the subject is in combination with surgery. In some embodiments, administering the adenovirus or the pharmaceutical composition described herein to the subject is in combination with radiation. In some embodiments, administering the adenovirus or the pharmaceutical composition described herein to the subject is in combination with chemotherapy. In some embodiments, administering the adenovirus or the pharmaceutical composition described herein to the subject is in combination with immunotherapy. In some embodiments, administering the adenovirus or the pharmaceutical composition described herein to the subject is in combination with hormone therapy. Examples of chemotherapeutic agents for chemotherapy are listed above.

In some embodiments, the replication competent recombinant adenovirus described herein can be formulated into a vaccine. The term "vaccine" as used herein can refer to a composition that comprises a replication competent recombinant adenovirus described herein and a carrier. In some embodiments, the carrier is an adjuvant. Examples of the adjuvant include, but are not limited to, salts (e.g., calcium phosphate, aluminum phosphate, calcium hydroxide, or aluminum hydroxide); natural polymers (e.g., algal glucans such as beta glucans), chitosan or crystallized inulin; synthetic polymers (e.g., poly-lactides, poly-glycolides, poly lacitide-co-glycolides, or methylacrylate polymers); micelle-forming cationic or non-ionic block copolymers or surfactants (e.g., Pluronics, L121, L122, L123, Tween 80, or NP-40); fatty acid, lipid or lipid and protein based vesicles (e.g., liposomes, proteoliposomes, ISCOM, or cochleate structures); and surfactant stabilized emulsions composed of synthetic or natural oils and aqueous solutions. In some embodiments, the vaccine comprising a replication competent recombinant adenovirus described herein can ameliorate at least one symptom of a disease or a disorder such as cancer. For example, in some embodiments, the vaccine comprising a replication competent recombinant adenovirus described herein can induce a therapeutic effect of a protein encoded by a heterologous sequence or induce oncolysis such that symptoms and/or complications of cancer will be alleviated, reduced, or improved in a subject suffering from a cancer.

The subjects that can be treated with the replication competent recombinant adenovirus and methods described herein can be any subject with a proliferative disorder such as cancer. For example, the subject may be a eukaryotic subject, such as an animal. In some embodiments, the subject is a mammal, e.g., human. In some embodiments, the subject is a human. In some embodiments, the subject is a non-human animal. In some embodiments, the subject is a fetus, an embryo, or a child. In some embodiments, the subject is a non-human primate such as chimpanzee, and other apes and monkey species; farm animals such as cattle, horses, sheep, goats, pigs; domestic animals such as rabbits, dogs, and cats; laboratory animals including rodents, such as rats, mice, and guinea pigs, and the like.

In some embodiments, the subject is prenatal (e.g., a fetus), a child (e.g., a neonate, an infant, a toddler, a preadolescent), an adolescent, a pubescent, or an adult (e.g., an early adult, a middle-aged adult, a senior citizen). The human subject can be between about 0 month and about 120 years old, or older. The human subject can be between about 0 and about 12 months old; for example, about 1, 2, 3, 4, 5, 6, 7, 8, 9, 10, 11, or 12 months old. The human subject can be between about 0 and 12 years old; for example, between about 0 and 30 days old; between about 1 month and 12 months old; between about 1 year and 3 years old; between about 4 years and 5 years old; between about 4 years and 12 years old; about 1, 2, 3, 4, 5, 6, 7, 8, 9, 10, 11, or 12 years old. The human subject can be between about 13 years and 19 years old; for example, about 13, 14, 15, 16, 17, 18, or 19 years old. The human subject can be between about 20 and about 39 years old; for example, about 20, 21, 22, 23, 24, 25, 26, 27, 28, 29, 30, 31, 32, 33, 34, 35, 36, 37, 38, or 39 years old. The human subject can be between about 40 to about 59 years old; for example, about 40, 41, 42, 43, 44, 45, 46, 47, 48, 49, 50, 51, 52, 53, 54, 55, 56, 57, 58, or 59 years old. The human subject can be greater than 59 years old; for example, about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 years old. The human subjects can include male subjects and/or female subjects.

EXAMPLES

The present disclosure will be described in greater detail by way of specific examples. These examples are provided for illustrative purposes only and not to limit the scope of the claims provided herein. Those of skill in the art will readily recognize a variety of non-critical parameters that can be changed or modified to yield alternative embodiments according to the present disclosure.

Example 1: Vector Construction and Cloning

Electrocompetent BJ5183 cells are prepared in 20 microliter aliquots. 100-500 ng of pShuttle plasmids are linearized with I-CeuI and PI-SceI. After digestion, DNAs are phenol-chloroform extracted, ethanol precipitated, and resuspended in 6.0 microliters of ddH2O. digested shuttle plasmid with 1.0 microliter of recombinant adenoviral backbone vector (100 ng/μl) are co-transformed. Twenty microliters of electrocompetent *E. coli* BJ5183 cells are added and electroporation is performed in 2.0 mm cuvettes at 2,500V, 200 Ohms, and 25 micro-FD in a Bio-Rad Gene Pulser electroporator. Transformation mix is resuspended in 500 microliters of L-broth and plated on LB/Kan plates, and grown at 37° C. overnight (16-20 hrs). 10 to 20 smallest colonies are picked up and grown in 2 ml L-broth containing 25 μg/mL kanamycin for 10-15 hours. Miniprep is performed using alkaline lysis method, and supercoiled plasmids are checked by running miniprep on 0.8% agarose gel. Correct clones are checked with restriction digestion with PacI, and correct recombinant vectors are re-transformed for miniprep. Plasmids are purified by CsCl-binding.

The examples and embodiments described herein are for illustrative purposes only and various modifications or changes suggested to persons skilled in the art are to be included within the spirit and purview of this application and scope of the appended claims.

What is claimed is:

1. A replication competent recombinant oncolytic adenovirus comprising restriction sites comprising an I-CeuI restriction site, a PI-SceI restriction site, or a combination thereof in an E3 region, wherein the E3 region does not comprise a deletion as compared to a wild type adenovirus of the same serotype.

2. The replication competent recombinant oncolytic adenovirus of claim 1, wherein the restriction sites of E3 region comprise the I-CeuI restriction site and the PI-SceI restriction site.

3. The replication competent recombinant oncolytic adenovirus of claim 2, further comprising a heterologous nucleotide sequence located between the I-CeuI restriction site and the PI-SceI restriction site.

4. The replication competent recombinant oncolytic adenovirus of claim 3, wherein the heterologous nucleotide sequence is cloned from a shuttle vector.

5. The replication competent recombinant oncolytic adenovirus of claim 4, wherein the shuttle vector is a pShuttle or pShuttleX vector.

6. The replication competent recombinant oncolytic adenovirus of claim 3, wherein the heterologous nucleotide sequence comprises a gene.

7. The replication competent recombinant oncolytic adenovirus of claim 6, wherein the gene encodes a cytokine, a chemokine, a checkpoint inhibitor, or an interleukin.

8. The replication competent recombinant oncolytic adenovirus of claim 6, wherein the heterologous nucleotide sequence comprises a Reduced Expression in Immortalized Cells (REIC) gene sequence or an Interleukin-2 (IL-2) gene sequence.

9. The replication competent recombinant oncolytic adenovirus of claim 5, further comprising an exogenous promoter operably linked to the E3 region, the E1 region, or the heterologous nucleotide sequence.

10. The replication competent recombinant oncolytic adenovirus of claim 9, wherein the exogenous promoter comprises (i) a tissue specific promoter or (ii) a CAG promoter system.

11. The replication competent recombinant oncolytic adenovirus of claim 1, wherein the restriction sites of E3 region consist of the I-CeuI restriction site and the PI-SceI restriction site.

12. The replication competent recombinant oncolytic adenovirus of claim 1, wherein further comprising an E1 region, wherein (i) the E1 region comprises a same sequence as compared to a wild type adenovirus of the same serotype; (ii) the E1 region comprises a partial deletion compared to a wild type adenovirus of the same serotype; (iii) the E1 region of the adenovirus does not contain an insertion of a heterologous nucleotide sequence; and/or (iv) the E1 region comprises an E1B-55k deletion.

13. The replication competent recombinant oncolytic adenovirus of claim 1, wherein the adenovirus further comprises a modification in an E1a, E1b, E2, or E4 gene.

14. The replication competent recombinant oncolytic adenovirus of claim 1, further comprising a polynucleotide sequence encoding a modified adenoviral fiber protein.

15. The replication competent recombinant oncolytic adenovirus of claim 14, wherein the modified adenoviral fiber protein is an Ad35 fiber tail protein.

16. The replication competent recombinant oncolytic adenovirus of claim 1, wherein the adenovirus is selected from the group consisting of adenovirus type 2, adenovirus type 4, adenovirus type 5, and adenovirus type 7.

17. The replication competent recombinant oncolytic adenovirus of claim 1, wherein the adenovirus preferentially replicates in a tumor cell as compared to a non-tumor cell.

18. The replication competent recombinant oncolytic adenovirus of claim 17, wherein the tumor cell comprises a mutation in a p53 gene or a reduced level of the p53 gene expression as compared to a non-tumor cell.

19. A composition, comprising the replication competent recombinant oncolytic adenovirus of claim 1.

* * * * *